United States Patent
Mao et al.

(10) Patent No.: US 11,414,689 B2
(45) Date of Patent: Aug. 16, 2022

(54) HYDROLYSIS OF STEVIOL GLYCOSIDES BY BETA-GLUCOSIDASE

(71) Applicant: Conagen Inc., Bedford, MA (US)

(72) Inventors: Guohong Mao, Burlington, MA (US); Jacob Edward Vick, Cambridge, MA (US); Michael Batten, Westford, MA (US); Oliver Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 100 days.

(21) Appl. No.: 16/725,242

(22) Filed: Dec. 23, 2019

(65) Prior Publication Data

US 2020/0291441 A1 Sep. 17, 2020

Related U.S. Application Data

(63) Continuation of application No. PCT/US2018/040193, filed on Jun. 29, 2018.

(60) Provisional application No. 62/527,482, filed on Jun. 30, 2017.

(51) Int. Cl.
*C12P 19/56* (2006.01)

(52) U.S. Cl.
CPC ....... *C12P 19/56* (2013.01); *C12Y 302/01023* (2013.01)

(58) Field of Classification Search
CPC .............................. C07H 1/00; C07H 15/256; C12Y 302/01015; C12Y 302/01023; C12Y 302/01021; A23L 5/25; A23L 27/36; C12P 19/56; C12P 19/14
See application file for complete search history.

(56) References Cited

U.S. PATENT DOCUMENTS

| | | | |
|---|---|---|---|
| 9,522,929 B2 | 12/2016 | Mao et al. | |
| 9,527,880 B2 | 12/2016 | Mao et al. | |
| 9,567,619 B2 | 2/2017 | Mao et al. | |
| 9,643,990 B2 | 5/2017 | Mao et al. | |
| 9,765,104 B2 | 9/2017 | Mao et al. | |
| 9,783,566 B2 | 10/2017 | Mao et al. | |
| 9,850,270 B2 | 12/2017 | Mao et al. | |
| 9,908,913 B2 | 3/2018 | Mao et al. | |
| 9,988,414 B2 | 6/2018 | Mao et al. | |
| 10,010,099 B2 | 7/2018 | Mao et al. | |
| 10,010,101 B2 | 7/2018 | Mao et al. | |
| 10,023,604 B2 | 7/2018 | Mao et al. | |
| 10,059,732 B2 | 8/2018 | Mao et al. | |
| 10,081,826 B2 | 9/2018 | Mao et al. | |
| 10,138,263 B2 | 11/2018 | Mao et al. | |
| 10,160,781 B2 | 12/2018 | Mao et al. | |
| 10,253,344 B2 | 4/2019 | Mao et al. | |
| 10,724,062 B2 * | 7/2020 | Mao | C12N 15/74 |
| 11,098,315 B2 | 8/2021 | Mao et al. | |
| 2011/0091634 A1 | 4/2011 | Abelyan et al. | |
| 2014/0329281 A1 | 11/2014 | Houghton-Larsen et al. | |
| 2016/0088865 A1 | 3/2016 | Berry | |
| 2016/0095338 A1 | 4/2016 | Mao et al. | |
| 2016/0183574 A1 | 6/2016 | Chen et al. | |
| 2016/0186225 A1 | 6/2016 | Mikkelsen et al. | |
| 2016/0251635 A1 | 9/2016 | Mao et al. | |
| 2016/0298159 A1 | 10/2016 | Tao et al. | |
| 2017/0362267 A1 | 12/2017 | Mao et al. | |
| 2018/0009835 A1 | 1/2018 | Mao et al. | |
| 2018/0037600 A1 | 2/2018 | Mao et al. | |
| 2018/0057519 A1 | 3/2018 | Mao et al. | |
| 2018/0057520 A1 | 3/2018 | Mao et al. | |
| 2018/0057521 A1 | 3/2018 | Mao et al. | |
| 2018/0057522 A1 | 3/2018 | Mao et al. | |
| 2018/0244709 A1 | 8/2018 | Mao et al. | |
| 2018/0258124 A1 | 9/2018 | Mao et al. | |
| 2018/0258125 A1 | 9/2018 | Mao et al. | |
| 2018/0258126 A1 | 9/2018 | Mao et al. | |
| 2019/0078102 A1 | 3/2019 | Mao et al. | |
| 2019/0345528 A1 | 11/2019 | Mao et al. | |
| 2021/0002685 A1 | 1/2021 | Mao et al. | |
| 2022/0042060 A1 | 2/2022 | Mao et al. | |

FOREIGN PATENT DOCUMENTS

| | | |
|---|---|---|
| EP | 2957182 A1 | 12/2015 |
| WO | WO 2013/026151 A1 | 2/2013 |
| WO | WO 2014/193934 A1 | 12/2014 |
| WO | WO 2016/073740 A1 | 11/2015 |
| WO | WO 2016/043926 A1 | 3/2016 |
| WO | WO 2016/054540 A1 | 4/2016 |
| WO | WO 2016/120486 A1 | 8/2016 |
| WO | WO 2018/164747 A1 | 9/2018 |

OTHER PUBLICATIONS

Bhatia et al., Purification and characterization of recombinant *Escherichia coli*-expressed Pichia etchellsii β-glucosidase II with high hydrolytic activity on sophorose. Appl Microbiol Biotechnol (2005) 66: 527-535. (Year: 2005).*
Ko et al., Characterization of a novel steviol-producing β-glucosidase from Penicillium decumbens and optimal production of the steviol. Appl Microbiol Biotechnol (2013) 97:8151-8161. (Year: 2013).*
Nakano et al., Purification and Characterization of a Novel β-glucosidase from Clavibacter michiganense that Hydrolyzes Glucosyl Ester Linkage in Steviol Glycosides. Journal of Fermentation and Bioengineering vol. 85, No. 2, 162-168. 1998 (Year: 1998).*
Ohta et al., Characterization of Novel Steviol Glycosides from Leaves of Stevia rebaudiana Morita. J. Appl. Glycosci., 57, 199-209 (2010). (Year: 2010).*
Pandey et al., Cloning and Expression of β-glucosidase Gene from the Yeast Pichia etchellsii. Journal of Fermentation and Bioengineering, vol. 80, No. 5, 446-453. 1995 (Year: 1995).*
PCT/US2018/040193, Sep. 17, 2018, International Search Report and Written Opinion.

(Continued)

*Primary Examiner* — Ganapathirama Raghu
(74) *Attorney, Agent, or Firm* — Wolf, Greenfield & Sacks, P.C.; W. John Keyes

(57) ABSTRACT

The present disclosure relates to the use of beta-glucosidase to enhance the production efficiency of desired steviol glycosides, such as rebaudioside M (reb M).

18 Claims, 17 Drawing Sheets

Specification includes a Sequence Listing.

(56) References Cited

OTHER PUBLICATIONS

PCT/US2018/040193, Jan. 9, 2020, International Preliminary Report and Patentability.
International Search Report and Written Opinion for Application No. PCT/US2018/040193 dated Sep. 17, 2018.
International Preliminary Report and Patentability for Application No. PCT/US2018/040193 dated Jan. 9, 2020.
Wang et al., Selective production of rubusoside from stevioside by using the sophorose activity of β-glucosidase from Streptomyces sp. GXT6. Appl Microbiol Biotechnol. Nov. 2015;99(22):9663-74. doi: 10.1007/s00253-015-6802-z. Epub Jul. 22, 2015.
Brandle et al., Stevia Rebaudiana: Its Agricultural, Biological, and Chemical Properties. Canadian Journal of Plant Science. 1998;78(4):527-36.
Ceunen et al., Steviol Glycosides: Chemical Diversity, Metabolism, and Function. Journal of Natural Products. 2013;76 (6):1201-28.
Devos et al., Practical limits of function prediction. Proteins. Oct. 1, 2000;41(1):98-107.
Du et al., Engineering Microbial Factories for Synthesis of Value-Added Products. J Ind Microbiol Biotechnol. Aug. 2011;38(8):873-90. doi: 10.1007/s10295-011-0970-3. Epub Apr. 28, 2011.
Hausler et al., Microbial production of natural flavors. ASM NEWS. 1997;63:551-59.
Kisselev, Polypeptide release factors in prokaryotes and eukaryotes: same function, different structure. Structure. Jan. 2002;10(1):8-9. doi: 10.1016/s0969-2126(01)00703-1.
Prakash et al., Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita. Biomolecules. Jun. 2014; 4(2):374-89.
Prakash et al., Development of Next Generation Stevia Sweetener: Rebaudioside M. Foods. 2014;3:162-175.
Shockey et al., Arabidopsis contains a large superfamily of acyl-activating enzymes: phylogenetic and biochemical analysis reveals a new class of acyl-coenzyme A synthetases. Plant Physiol. 2003;132:1065-76.
Talha et al., Analysis of stevioside in Stevia rebaudiana, J. Med. Plants. Mar. 23, 2012; 6(11):2216-2219.
Whisstock et al., Prediction of protein function from protein sequence and structure. Q Rev Biophys. Aug. 2003;36(3):307-40. doi: 10.1017/s0033583503003901.
Witkowski et al., Conversion of a beta-ketoacyl synthase to a malonyl decarboxylase by replacement of the active-site cysteine with glutamine. Biochemistry. Sep. 7, 1999;3 8(36):11643-50. doi: 10.1021/bi990993h.
*U.S. Appl. No. 16/904,797, filed Jun. 18, 2020, Mao et al.
*U.S. Appl. No. 17/387,230, filed Jul. 28, 2021, Mao et al.
PCT/US2017/056457, Jan. 18, 2018, International Search Report and Written Opinion.
PCT/US2017/056457, Apr. 25, 2019, International Preliminary Report on Patentability.
EP17861012.7, Sep. 4, 2020, Extended European Search Report.

* cited by examiner

SEQUENCE LISTING

<160> NUMBER OF SEQ ID NOS: 8

<210> SEQ ID NO 1
<211> LENGTH: 839
<212> TYPE: PRT
<213> ORGANISM: Pichia pastoris

<400> SEQUENCE: 1

```
Met Thr Gln Leu Asp Val Glu Ser Leu Ile Gln Glu Leu Thr Leu Asn
1               5                   10                  15

Glu Lys Val Gln Leu Leu Ser Gly Ser Asp Phe Trp His Thr Thr Pro
            20                  25                  30

Val Arg Arg Leu Gly Ile Pro Lys Met Arg Leu Ser Asp Gly Pro Asn
        35                  40                  45

Gly Val Arg Gly Thr Lys Phe Phe Asn Gly Val Pro Thr Ala Cys Phe
    50                  55                  60

Pro Cys Gly Thr Gly Leu Gly Ala Thr Phe Asp Lys Glu Leu Leu Lys
65                  70                  75                  80

Glu Ala Gly Ser Leu Met Ala Asp Glu Ala Lys Ala Lys Ala Ala Ser
                85                  90                  95

Val Val Leu Gly Pro Thr Ala Asn Ile Ala Arg Gly Pro Asn Gly Gly
            100                 105                 110

Arg Gly Phe Glu Ser Phe Gly Glu Asp Pro Val Val Asn Gly Leu Ser
        115                 120                 125

Ser Ala Ala Met Ile Asn Gly Leu Gln Gly Lys Tyr Ile Ala Ala Thr
    130                 135                 140

Met Lys His Tyr Val Cys Asn Asp Leu Glu Met Asp Arg Asn Cys Ile
145                 150                 155                 160

Asp Ala Gln Val Ser His Arg Ala Leu Arg Glu Val Tyr Leu Leu Pro
                165                 170                 175

Phe Gln Ile Ala Val Arg Asp Ala Asn Pro Arg Ala Ile Met Thr Ala
            180                 185                 190

Tyr Asn Lys Ala Asn Gly Glu His Val Ser Gln Ser Lys Phe Leu Leu
        195                 200                 205

Asp Glu Val Leu Arg Lys Glu Trp Gly Trp Asp Gly Leu Leu Met Ser
    210                 215                 220

Asp Trp Phe Gly Val Tyr Asp Ala Lys Ser Ser Ile Thr Asn Gly Leu
225                 230                 235                 240

Asp Leu Glu Met Pro Gly Pro Pro Gln Cys Arg Val His Ser Ala Thr
                245                 250                 255

Asp His Ala Ile Asn Ser Gly Glu Ile His Ile Asn Asp Val Asp Glu
            260                 265                 270

Arg Val Arg Ser Leu Leu Ser Leu Ile Asn Tyr Cys His Gln Ser Gly
        275                 280                 285

Val Thr Glu Glu Asp Pro Glu Thr Ser Asp Asn Asn Thr Pro Glu Thr
    290                 295                 300

Ile Glu Lys Leu Arg Lys Ile Ser Arg Glu Ser Ile Val Leu Leu Lys
305                 310                 315                 320
```

```
Asp Asp Asp Arg Asn Arg Ser Ile Leu Pro Leu Lys Lys Ser Asp Lys
                325                 330                 335

Ile Ala Val Ile Gly Asn Asn Ala Lys Gln Ala Ala Tyr Cys Gly Gly
                340                 345                 350

Gly Ser Ala Ser Val Leu Ser Tyr His Thr Thr Thr Pro Phe Asp Ser
                355                 360                 365

Ile Lys Ser Arg Leu Glu Asp Ser Asn Thr Pro Ala Tyr Thr Ile Gly
                370                 375                 380

Ala Asp Ala Tyr Lys Asn Leu Pro Pro Leu Gly Pro Gln Met Thr Asp
385                 390                 395                 400

Ser Asp Gly Lys Pro Gly Phe Asp Ala Lys Phe Phe Val Gly Ser Pro
                405                 410                 415

Thr Ser Lys Asp Arg Lys Leu Ile Asp His Phe Gln Leu Thr Asn Ser
                420                 425                 430

Gln Val Phe Leu Val Asp Tyr Tyr Asn Glu Gln Ile Pro Glu Asn Lys
                435                 440                 445

Glu Phe Tyr Val Asp Val Glu Gly Gln Phe Ile Pro Glu Glu Asp Gly
    450                 455                 460

Thr Tyr Asn Phe Gly Leu Thr Val Phe Gly Thr Gly Arg Leu Phe Val
465                 470                 475                 480

Asp Asp Lys Leu Val Ser Asp Ser Ser Gln Asn Gln Thr Pro Gly Asp
                485                 490                 495

Ser Phe Phe Gly Leu Ala Ala Gln Glu Val Ile Gly Ser Ile His Leu
                500                 505                 510

Val Lys Gly Lys Ala Tyr Lys Ile Lys Val Leu Tyr Gly Ser Ser Val
                515                 520                 525

Thr Arg Thr Tyr Glu Ile Ala Ala Ser Val Ala Phe Glu Gly Gly Ala
                530                 535                 540

Phe Thr Phe Gly Ala Ala Lys Gln Arg Asn Glu Asp Glu Glu Ile Ala
545                 550                 555                 560

Arg Ala Val Glu Ile Ala Lys Ala Asn Asp Lys Val Val Leu Cys Ile
                565                 570                 575

Gly Leu Asn Gln Asp Phe Glu Ser Glu Gly Phe Asp Arg Pro Asp Ile
                580                 585                 590

Lys Ile Pro Gly Ala Thr Asn Lys Met Val Ser Ala Val Leu Lys Ala
                595                 600                 605

Asn Pro Asn Thr Val Ile Val Asn Gln Thr Gly Thr Pro Val Glu Met
                610                 615                 620

Pro Trp Ala Ser Asp Ala Pro Val Ile Leu Gln Ala Trp Phe Gly Gly
625                 630                 635                 640

Ser Glu Ala Gly Thr Ala Ile Ala Asp Val Leu Phe Gly Asp Tyr Asn
                645                 650                 655

Pro Ser Gly Lys Leu Thr Val Thr Phe Pro Leu Arg Phe Glu Asp Asn
                660                 665                 670

Pro Ala Tyr Leu Asn Phe Gln Ser Asn Lys Gln Ala Cys Trp Tyr Gly
                675                 680                 685

Glu Asp Val Tyr Val Gly Tyr Arg Tyr Glu Thr Ile Asp Arg Pro
                690                 695                 700

Val Leu Phe Pro Phe Gly His Gly Leu Ser Phe Thr Glu Phe Asp Phe
705                 710                 715                 720

Thr Asp Met Phe Val Arg Leu Glu Glu Glu Asn Leu Glu Val Glu Val
                725                 730                 735
```

```
Val Val Arg Asn Thr Gly Lys Tyr Asp Gly Ala Glu Val Val Gln Leu
            740                 745                 750

Tyr Val Ala Pro Val Ser Pro Ser Leu Lys Arg Pro Ile Lys Glu Leu
        755                 760                 765

Lys Glu Tyr Ala Lys Ile Phe Leu Ala Ser Gly Glu Ala Lys Thr Val
        770                 775                 780

His Leu Ser Val Pro Ile Lys Tyr Ala Thr Ser Phe Phe Asp Glu Tyr
785                 790                 795                 800

Gln Lys Lys Trp Cys Ser Glu Lys Gly Glu Tyr Thr Ile Leu Leu Gly
            805                 810                 815

Ser Ser Ser Ala Asp Ile Lys Val Ser Gln Ser Ile Thr Leu Glu Lys
            820                 825                 830

Thr Thr Phe Trp Lys Gly Leu
            835
```

<210> SEQ ID NO 2
<211> LENGTH: 2520
<212> TYPE: DNA
<213> ORGANISM: Artificial Seq
<220> FEATURE:
<223> OTHER INFORMATION: Synthetic polynucleotide

<400> SEQUENCE: 2

```
atgacccaac tggatgtgga gagcctgatt caagagctga ccctgaacga aaaggtgcaa      60
ctgctgagcg gtagcgactt ctggcatacc accccggttc gtcgtctggg catcccgaag     120
atgcgtctga gcgacggtcc gaacggcgtt cgtggtacca aattctttaa cggtgttccg     180
accgcgtgct cccgtgcgg taccggtctg gcgcgacct ttgacaagga actgctgaaa       240
gaggcgggta gcctgatggc ggatgaagcg aaagcgaaag cggcgagcgt ggttctgggt     300
ccgaccgcga acattgcgcg tggtccgaac ggtggccgtg gcttcgagag cttcggcgag     360
gacccggtgg ttaacggtct gagcagcgcg gcgatgatca acggcctgca gggcaagtac     420
attgcggcga ccatgaaaca ctatgttttgc aacgatctgg aaatggaccg taactgcatt    480
gacgcgcaag ttagccaccg tgcgctgcgt gaggtgtacc tgctgccgtt ccaaatcgcg     540
gtgcgtgatg cgaacccgcg tgcgattatg accgcgtata caaggcgaa cggcgaacac     600
gttagccaga gcaaattcct gctggacgaa gtgctgcgta aggagtgggg ctgggatggt     660
ctgctgatga gcgactggtt tggtgtttac gatgcgaaaa gcagcatcac caacggcctg     720
gacctggaga tgccggggtcc gccgcagtgc cgtgtgcaca gcgcgaccga tcacgcgatc     780
aacagcggcg aaatccacat taacgatgtt gacgagcgtg tgcgtagcct gctgagcctg     840
attaactact gccaccaaag cggtgttacc gaggaagatc cggaaaccag cgacaacaac     900
accccggaaa ccatcgagaa gctgcgtaaa atcagccgtg agagcattgt gctgctgaag     960
gacgatgacc gtaaccgtag cattctgccg ctgaagaaaa gcgacaaaat cgcggttatt    1020
ggtaacaacg cgaaacaagc ggcgtattgc ggtggcggta cgcgagcgt gctgagctat     1080
cacaccacca ccccgttcga cagcatcaag agccgtctgg aagatagcaa caccccggcg    1140
tacaccattg gtgcggacgc gtataaaaac ctgccgccgc tgggtccgca aatgaccgat    1200
agcgacggca agccgggttt tgatgcgaaa ttctttgttg cagcccgac cagcaaggat     1260
cgtaaactga tcgaccactt ccagctgacc aacagccaag ttttctctgg ggactactat     1320
aacgaacaga tcccggaaaa caaggagttc tacgttgacg tggagggtca atttattccg    1380
gaggaagatg gcacctataa cttcggtctg accgtgttgt gtaccggccg tctgttcgtt    1440
```

```
gatgacaaac tggttagcga cagcagccag aaccaaaccc cgggcgatag cttctttggt    1500
ctggcggcgc aggaagtgat cggcagcatt cacctggtga agggtaaagc gtacaagatc    1560
aaagttctgt atggcagcag cgtgacccgt acctacgaaa ttgcggcgag cgttgcgttt    1620
gagggcggtg cgttcacctt tggtgcggcg aaacagcgta acgaagacga ggaaatcgcg    1680
cgtgcggtgg agattgcgaa ggcgaacgac aaagtggttc tgtgcatcgg cctgaaccaa    1740
gatttcgaaa gcgagggttt tgatcgtccg gacatcaaga ttccgggcgc gaccaacaaa    1800
atggttagcg cggtgctgaa ggcgaacccg aacaccgtta ttgtgaacca gaccggtacc    1860
ccggttgaga tgccgtgggc gagcgatgcg ccggtgatcc tgcaagcgtg gtttggcggt    1920
agcgaggcgg gtaccgcgat tgcggatgtt ctgtttggcg actacaaccc gagcggcaag    1980
ctgaccgtga ccttcccgct gcgttttgag gataacccgg cgtacctgaa cttccagagc    2040
aacaaacaag cgtgctggta tggcgaagac gtttacgtgg ttatcgtta ctatgagacc    2100 atcgatcgtc cggtgctgtt cccgtttggt cacggcctga gcttcaccga gttcgatttt    2160
accgacatgt ttgttcgtct ggaggaagag aacctggaag ttgaggtggt tgtgcgtaac    2220
accggcaagt acgacggtgc ggaagtggtg cagctgtatg ttgcgccggt tagcccgagc    2280
ctgaaacgtc cgatcaagga actgaaagag tacgcgaaaa ttttcctggc gagcggtgaa    2340
gcgaagaccg ttcacctgag cgtgccgatc aaatacgcga ccagcttctt tgatgagtat    2400
caaaagaaat ggtgcagcga aaagggcgag tataccattc tgctgggtag cagcagcgcg    2460
gacatcaaag ttagccaaag catcacccctg gaaaaaacca ccttctggaa aggtctgtaa    2520
```

```
<210> SEQ ID NO 3
<211> LENGTH: 346
<212> TYPE: PRT
<213> ORGANISM: Pichia pastoris

<400> SEQUENCE: 3

Met Lys Ser Gln Leu Ile Phe Met Ala Leu Ala Ser Leu Val Ala Ser
1               5                   10                  15

Ala Pro Leu Glu His Gln Gln Gln His His Lys His Glu Lys Arg Ala
                20                  25                  30

Val Val Thr Gln Thr Val Thr Val Ala Ala Gly Gln Thr Ala Ala Ala
            35                  40                  45

Gly Ser Ala Gln Ala Val Val Thr Ser Ser Ala Pro Ala Ser Val
        50                  55                  60

Ala Ser Ser Ala Ala Ala Ser Ala Ser Ser Ser Ser Ser Tyr Thr
65                  70                  75                  80

Ser Gly Ala Ser Gly Asp Leu Ser Ser Phe Lys Asp Gly Thr Ile Lys
                85                  90                  95

Cys Ser Glu Phe Pro Ser Gly Asp Gly Val Val Ser Val Ser Trp Leu
                100                 105                 110

Gly Phe Gly Gly Trp Ser Ser Ile Met Asn Leu Gln Gly Gly Thr Ser
            115                 120                 125

Glu Ser Cys Glu Asn Gly Tyr Tyr Cys Ser Tyr Ala Cys Glu Ala Gly
        130                 135                 140

Tyr Ser Lys Thr Gln Trp Pro Ser Asn Gln Pro Ser Asp Gly Arg Ser
145                 150                 155                 160

Val Gly Gly Leu Leu Cys Lys Asp Gly Leu Leu Tyr Arg Ser Asn Thr
                165                 170                 175

Ala Phe Asp Thr Leu Cys Val Pro Gly Lys Gly Thr Ala Ser Val Glu
                180                 185                 190
```

Asn Asn Val Ser Lys Gly Ile Ser Ile Cys Arg Thr Asp Tyr Pro Gly
            195                 200                 205

Ser Glu Asn Met Cys Val Pro Thr Trp Val Asp Ala Gly Asn Ser Asn
    210                 215                 220

Thr Leu Thr Val Val Asp Glu Asp Asn Tyr Tyr Glu Trp Gln Gly Leu
225                 230                 235                 240

Lys Thr Ser Ala Gln Tyr Tyr Val Asn Asn Ala Gly Val Ser Val Glu
                245                 250                 255

Asp Gly Cys Ile Trp Gly Asp Glu Ser Ser Gly Val Gly Asn Trp Ala
            260                 265                 270

Pro Leu Val Leu Gly Ala Gly Ser Thr Gly Gly Leu Thr Tyr Leu Ser
    275                 280                 285

Leu Ile Pro Asn Pro Asn Asn Lys Lys Ala Pro Asn Phe Asn Val Lys
290                 295                 300

Ile Val Ala Thr Asp Gly Ser Ser Ile Asn Gly Asp Cys Lys Tyr Glu
305                 310                 315                 320

Asn Gly Ile Phe Val Gly Ser Ser Thr Asp Gly Cys Thr Val Thr Val
                325                 330                 335

Thr Ser Gly Ser Ala Lys Leu Val Phe Tyr
            340                 345

<210> SEQ ID NO 4
<211> LENGTH: 1041
<212> TYPE: DNA
<213> ORGANISM: Pichia pastoris

<400> SEQUENCE: 4
atgaaaagcc agctgatctt tatggctttg gcctcccttg tagcaagtgc accgctggaa     60
caccagcagc agcatcataa acatgagaaa cgcgccgtag ttacgcagac agtaactgtt    120
gcggcgggcc agacagcagc agcgggttcc gcccaggcag ttgttacctc aagcgcggcg    180
ccagcatccg ttgcttcaag tgcggccgcg tctgctagct catcttcttc cagctatacc    240
tctggcgctt caggcgatct tagtagtttc aaagatggta ctattaaatg ttcagaattc    300
ccatcagggg atggcgtggt gtccgtctct tggttaggct tcggcggctg gtctagtatt    360
atgaatctgc agggtggtac ttcagagagt tgtgagaacg ctattattg ttcatatgca    420 tgtgaagccg ttatagcaa acacagtgg ccatctaacc agccgtcaga tgggagatca    480
gtgggagggt tgctgtgtaa agatggcctg ttatatcgct ccaatacagc gttcgataca    540
ttatgtgtgc ctggaaaagg tacagcatcc gtggagaata atgtgtctaa aggtattccc    600
atttgtagaa cggattatcc ggggtctgaa acatgtgcg tcccgacgtg ggtcgatgcc    660
ggtaactcaa acaccttgac agtggtagat gaagataatt attatgaatg caggggcctt    720
aaaactagtg ctcagtatta tgtgaataac gccggtgtta gtgttgaaga tgggtgcatc    780
tggggcgatg agtccagcgg cgttggaaac tgggcgccgt tggttttggg gccggttcc    840 acggggggtc tgacctatct gtctctgatt ccgaatccaa acaacaaaaa agcaccgaat    900
tttaacgtaa aaatcgtggc cacggatgga agttcaatta cggagattg caaatatgaa    960 aatgggatct tgtcggttc ttcaaccgat ggctgcacgg taactgttac ctcaggtagt   1020
gcaaaactgg ttttttatta a                                             1041

<210> SEQ ID NO 5
<211> LENGTH: 348
<212> TYPE: PRT

<213> ORGANISM: Pichia pastoris

<400> SEQUENCE: 5

```
Met Gln Val Lys Ser Ile Val Asn Leu Leu Leu Ala Cys Ser Leu Ala
1               5                   10                  15

Val Ala Arg Pro Leu Glu His Ala His His Gln His Asp Lys Arg Gly
            20                  25                  30

Val Val Val Thr Lys Thr Ile Val Val Asp Gly Ser Thr Val Glu
        35                  40                  45

Ala Thr Ala Ala Ala Gln Val Gln Glu His Ala Glu Thr Phe Ala Glu
    50                  55                  60

Ser Thr Pro Ser Ala Val Val Ser Ser Ser Ala Pro Ser Ser Ala
65                  70                  75                  80

Ser Ser Ala Ser Ala Pro Ala Ser Ser Gly Ser Phe Ser Ala Gly Thr
                85                  90                  95

Lys Gly Val Thr Tyr Ser Pro Tyr Gln Ala Gly Gly Cys Lys Thr
            100                 105                 110

Ala Glu Glu Val Ala Ser Asp Leu Ser Gln Leu Thr Gly Tyr Glu Ile
        115                 120                 125

Ile Arg Leu Tyr Gly Val Asp Cys Asn Gln Val Glu Asn Val Phe Lys
    130                 135                 140

Ala Lys Ala Pro Gly Gln Lys Leu Phe Leu Gly Ile Phe Phe Val Asp
145                 150                 155                 160

Ala Ile Glu Ser Gly Val Ser Ala Ile Ala Ser Ala Val Lys Ser Tyr
                165                 170                 175

Gly Ser Trp Asp Asp Val His Thr Val Ser Val Gly Asn Glu Leu Val
            180                 185                 190

Asn Asn Gly Glu Ala Thr Val Ser Gln Ile Gly Gln Tyr Val Ser Thr
        195                 200                 205

Ala Lys Ser Ala Leu Arg Ser Ala Gly Phe Thr Gly Pro Val Leu Ser
    210                 215                 220

Val Asp Thr Phe Ile Ala Val Ile Asn Asn Pro Gly Leu Cys Asp Phe
225                 230                 235                 240

Ala Asp Glu Tyr Val Ala Val Asn Ala His Ala Phe Phe Asp Gly Gly
                245                 250                 255

Ile Ala Ala Ser Gly Ala Gly Asp Trp Ala Glu Gln Ile Gln Arg
            260                 265                 270

Val Ser Ser Ala Cys Gly Gly Lys Asp Val Leu Ile Val Glu Ser Gly
        275                 280                 285

Trp Pro Ser Lys Gly Asp Thr Asn Gly Ala Ala Val Pro Ser Lys Ser
    290                 295                 300

Asn Gln Gln Ala Ala Val Gln Ser Leu Gly Gln Lys Ile Gly Ser Ser
305                 310                 315                 320

Cys Ile Ala Phe Asn Ala Phe Asn Asp Tyr Trp Lys Ala Asp Gly Pro
                325                 330                 335

Phe Asn Ala Glu Lys Tyr Trp Gly Ile Leu Asp Ser
            340                 345
```

<210> SEQ ID NO 6
<211> LENGTH: 1047
<212> TYPE: DNA
<213> ORGANISM: Pichia pastoris

<400> SEQUENCE: 6

```
atgcaggtta aatctattgt taatttactg cttgcctgtt ccttggctgt ggcgcgtccg    60
```

```
ttggaacacg ctcaccatca gcatgataaa cgcggcgttg tagtagtaac gaaaaccatc    120
gtcgttgatg gtagcacagt tgaggctacc gccgctgctc aggtgcagga gcatgcagaa    180
acctttgcag aatcaacccc gtcagccgtc gtttccagtt catccgcccc ttcatcagca    240
agctcagctt ccgctccagc tagttcaggt tcttttcag ctggtaccaa aggcgtgaca     300
tattctccat atcaggccgg tggtgggtgt aaaacagcgg aagaagtggc atccgatctg    360
tcacagctta ccggttatga aattattcgg ctttatggcg tagattgcaa ccaggttgag    420
aacgtgttta agccaaagc ccctggccag aaactttttt tgggtatctt ttttgtggat     480
gccatcgagt ctggcgtatc agctatcgca agtgccgtta atcctatgg ttcttgggat     540 gatgtacaca ctgtatctgt tggcaacgag ctggtgaaca atggcgaagc cactgttagc    600
cagattggac agtatgttag tacgccaaaa tcagccttac gctctgccgg tttcacaggg    660
ccagtattgt ctgttgatac ttttattgca gtgattaaca atccggggct gtgtgatttc    720
gcggatgaat atgttgctgt gaacgcccat gcgttcttcg atgggggtat tgctgcctca    780
ggggcgggcg attgggcggc agagcagatc cagcgcgtct ccagtgcgtg cggcgggaaa    840
gatgtcttaa ttgtagaaag cggttggccg tctaaaggag atacgaacgg cgccgcagtg    900
ccgtcaaaat ccaatcagca ggctgcagtc cagagtcttg ccagaaaat tgggagctca     960 tgcattgcct ttaacgcatt taatgattat tggaaagccg atggtccgtt caacgccgaa   1020
aaatattggg ggatccttga tagttaa                                       1047

<210> SEQ ID NO 7
<211> LENGTH: 464
<212> TYPE: PRT
<213> ORGANISM: Pichia pastoris

<400> SEQUENCE: 7

Met Leu Ser Thr Ile Leu Asn Ile Phe Ile Leu Leu Phe Ile Gln
1               5                   10                  15

Ala Ser Leu Gln Ala Pro Ile Pro Val Val Thr Lys Tyr Val Thr Glu
            20                  25                  30

Gly Ile Ala Val Val Thr Glu Thr Asn Val Arg Val Val Thr Lys Thr
        35                  40                  45

Ile Pro Ile Val Gln Val Leu Ile Ser Asp Gly Ala Thr Tyr Thr His
    50                  55                  60

Thr Leu Thr Thr Val Ser Thr Ala Glu Glu Asn Gly Asn Phe Gln Pro
65                  70                  75                  80

Ile Thr Thr Thr Ser Ile Val Asn Lys Glu Val Val Pro Thr Ser
                85                  90                  95

Val Thr Pro Asn Thr Gln Gln Thr Arg Pro Gln Val Asp Thr Thr
            100                 105                 110

Gln Asn Asn Ala Asp Thr Pro Ala Ala Pro Thr Pro Ser Pro Thr Thr
        115                 120                 125

Ser Ser Asn Asn Gly Val Phe Thr Thr Tyr Ser Thr Thr Arg Ser Val
    130                 135                 140

Val Thr Ser Val Val Val Gly Pro Asp Gly Ser Pro Ile Glu Asn
145                 150                 155                 160

Thr Gly Gln Thr Ala Asn Pro Thr Thr Thr Ala Pro Thr Thr Ser Thr
                165                 170                 175

Thr Ala Ala Arg Thr Thr Ser Ser Thr Ser Thr Thr Pro Thr Ala Ser
            180                 185                 190
```

Ser Thr Pro Gly Gly Asn His Pro Arg Ser Ile Val Tyr Ser Pro Tyr
            195                 200                 205

Ser Asp Ser Ser Gln Cys Lys Asp Ala Thr Thr Ile Glu Thr Asp Leu
        210                 215                 220

Glu Phe Ile Ala Ser Lys Gly Ile Ser Ala Val Arg Ile Tyr Gly Asn
225                 230                 235                 240

Asp Cys Asn Tyr Leu Thr Val Val Leu Pro Lys Cys Ala Ser Leu Gly
                245                 250                 255

Leu Lys Val Asn Gln Gly Phe Trp Ile Gly Pro Ser Gly Val Asp Ser
            260                 265                 270

Ile Asp Asp Ala Val Gln Glu Phe Ile Gln Ala Val Asn Gly Asn Asn
        275                 280                 285

Gly Phe Asn Trp Asp Leu Phe Glu Leu Ile Thr Val Gly Asn Glu Ala
290                 295                 300

Ile Ser Ala Gly Tyr Val Ser Ala Ser Ser Leu Ile Ser Lys Ile Lys
305                 310                 315                 320

Glu Val Ser Ser Ile Leu Ser Ser Ala Gly Tyr Thr Gly Pro Ile Thr
            325                 330                 335

Thr Ala Glu Pro Pro Asn Val Tyr Glu Asp Tyr Gly Asp Leu Cys Ser
        340                 345                 350

Thr Asp Val Met Ser Ile Val Gly Val Asn Ala His Ser Tyr Phe Asn
355                 360                 365

Thr Leu Phe Ala Ala Ser Asp Ser Gly Ser Phe Val Lys Ser Gln Ile
            370                 375                 380

Glu Val Val Gln Lys Ala Cys Ser Arg Ser Asp Ile Thr Ile Ile Glu
385                 390                 395                 400

Thr Gly Tyr Pro Ser Gln Gly Ala Thr Asn Gly Lys Asn Val Pro Ser
                405                 410                 415

Lys Glu Asn Gln Lys Thr Ala Ile Phe Ser Ile Phe Glu Val Val Gly
            420                 425                 430

Thr Asp Val Thr Ile Leu Ser Thr Tyr Asp Asp Leu Trp Lys Asp Pro
        435                 440                 445

Gly Pro Tyr Gly Ile Glu Gln Phe Phe Gly Ala Ile Asp Leu Phe Ser
450                 455                 460

<210> SEQ ID NO 8
<211> LENGTH: 1395
<212> TYPE: DNA
<213> ORGANISM: Pichia pastoris

<400> SEQUENCE: 8
atgctgtcca caattctgaa tatttttatt cttctgttat tcatccaggc gtctcttcag      60
gcgcctattc cggtggtgac caaatatgtg accgaaggta ttgccgttgt gactgaaacc     120
aatgtgcggg ttgttactaa aaccattccg attgtgcagg tgctgatctc cgatggtgca     180
acctatactc ataccctgac gacagtgtca acggcggaag aaaatggcaa cttccagcct     240
attaccacga catctattgt caacaaagaa gttgtagtac aacaagcgt aaccccgaat      300 acccagcaga cgcgtccgac ccaggtagat accacacaga acaatgcgga tacaccagcg     360
gcgcctacac catcacctac tactagttca acaacggcg tgttcaccac atattccaca     420
acacgtagcg tagtcactag tgtagtcgta gtcggaccgg atggaagccc tattgaaaat     480
actggacaga cagcaaaccc tactacaact gccccaacta caagcactac tgctgcccgg     540
accacaagca gtacgtccac cacacctacc gctagctcta cgccaggagg taatcatcca     600

```
cgtagcatcg tctattctcc atattccgat agcagtcagt gtaaagatgc gacaacgatc    660
gaaaccgatc ttgagttcat tgcctctaaa ggcatcagcg cggtacgtat ttatggcaat    720
gattgtaact atcttacagt tgttttgcct aaatgtgcca gtctgggatt aaaagtgaat    780
cagggctttt ggattggtcc aagtggagta gatagcatcg atgatgcagt acaggagttt    840
attcaggcag tcaacggcaa caacggcttt aattgggatt tattcgaatt aattaccgtc    900
ggaaacgaag caatcagtgc cggttatgtt tcagcgagct ccctgatttc caaaattaaa    960
gaagtatcta gcattctgag ctccgcgggt tatactggtc caattaccac agccgaaccg   1020
cctaacgtat atgaggatta tggcgatctg tgctcaaccg atgtaatgtc catcgtgggt   1080
gtaaacgcgc attcctattt taatacccctt tttgcggcct ccgattcagg ttcatttgtg  1140
aaatcacaga tcgaagtagt ccagaaagca tgctcacgtt ccgatattac tattattgaa   1200
accgggtatc cgtcccaggg agctaccaat ggaaaaaacg ttcctagtaa agagaatcag   1260
aaaacagcga tttttcaat ctttgaggtc gttggaacag atgtaactat tcttagtact    1320
tatgatgatt tgtggaaaga tcctggaccg tatgggattg aacagtttt tggtgcgatc    1380 gatctttttt cttaa                                                     1395
```

HYDROLYSIS OF STEVIOL GLYCOSIDES BY BETA-GLUCOSIDASE

CROSS-REFERENCE TO RELATED APPLICATIONS

This application is a continuation of International Application No. PCT/US2018/040193, filed Jun. 29, 2018, which claims priority under 35 U.S.C. § 119(e) to U.S. Provisional Application No. 62/527,482, filed Jun. 30, 2017, the contents of each of which are incorporated herein by reference in their entirety.

FIELD OF THE INVENTION

The field of the invention relates to methods and processes that make the production of desirable steviol glycosides more efficient and less costly. More specifically, the present disclosure relates to the use of hydrolysis by beta-glucosidase to drive the production of steviol glycosides of interest via bioconversion.

BACKGROUND OF THE INVENTION

The present disclosure is focused on the conversion of identified substrates to steviol glycosides of interest. In particular, the present disclosure relates, in part, to the more efficient production of rebaudioside M ("Reb M") through the use of beta-glucosidase ("B-glu1") to hydrolyze specific substrates present in disrupted recombinant cells such as recombinant microbial cells.

Steviol glycosides are natural products isolated from *Stevia rebaudiana* leaves, and are widely used as high intensity, low-caloric sweeteners in food, feed and beverages. Naturally occurring steviol glycosides have the same base diterpene backbone structure (steviol) but differ in the number and structure of carbohydrate residue modifications (e.g. glucose, rhamnose, and xylose residues) at the C13 and C19 positions of the steviol backbone. Steviol glycosides with known structures include stevioside, rebaudioside A, rebaudioside B, rebaudioside C, rebaudioside D, rebaudioside E, rebaudioside F, rebaudioside M and dulcoside A. In terms of commercial utilization rebaudioside M itself has been generally regarded as safe ('GRAS' status) but is extremely difficult to source from extraction processes and requires significant microbial modifications to produce through microbial bioconversion alone.

On dry weight basis, stevioside, rebaudioside A, rebaudioside C, and dulcoside A, account for 9.1, 3.8, 0.6, and 0.30 percent of the total weight of the steviol glycosides in wild type *Stevia* leaves, respectively, while the other steviol glucosides, such as Reb M are present in significantly lower amounts. It is known to use recombinant microbial cells to produce steviol glycosides of interest, however, given the range of biochemical activity of specific enzymes it can occur that a variety of steviol glycosides can be produced from such microbial strain. In these situations, the disrupted cells of these strains may contain high amounts of stevioside (CAS no. 57817-89-7), rebaudioside A (CAS no. 58543-16-1) or other steviol glycosides where Reb M is the desired product. The amounts of these compounds range from about 10-20% for stevioside and about 5-10% for rebaudioside A with other minor constituents being present in the mixture.

As natural sweeteners, different steviol glycosides have different degrees of sweetness, 'mouth feel' and specific after-tastes associated with each rebaudioside species tested. Relative to table sugar (i.e., "sucrose") the sweetness of steviol glycosides is significantly higher. For example, stevioside is 100-150 times sweeter than sucrose but has a bitter after-taste as noted in taste tests, while rebaudiosides A and E are 250-450 times sweeter than sucrose and the after-taste is much better than stevioside, however, a noticeable after-taste is still present. Accordingly, the taste profiles of any *stevia* extracts are profoundly affected by the relative content of the steviol glycosides in the extract, which in turn may are affected by the environmental conditions experienced by the underlying plants and the extraction process used. These variations in plant production, weather conditions and extraction conditions can lead to inconsistent compositions of the steviol glycosides in the *stevia* extracts, such that the taste profile varies strongly among different batches of extraction products. The taste profile of *stevia* extracts also can be affected by plant-derived or environment derived contaminants (such as pigments, lipids, proteins, phenolics and saccharides) that remain in the product after the extractions process. These contaminants typically have their own off-flavors undesirable for the use of the *stevia* extract as a sweetener in consumer products.

In addition, the cost of isolating individual or specific combinations of steviol glycosides that are not abundant in *stevia* extracts is cost and resource prohibitive. The non-biological production of steviol glycosides from stevioside and Reb A is difficult. Acid hydrolysis of stevioside is troublesome because under acidic conditions the steviol that is produced rearranges into isosteviol. Given that there is a limited quality and availability of some specific steviol glycosides, commercial supply can be better addressed by bio-conversion, where natural enzymes, or specific microbes can be modified to carry needed enzymes and use commercially significant fermentation processes to specifically increase the production of glycosides of interest. For example, bio-conversion of stevio side to Reb E has been reported previously (see, Mao et al., US Patent Application Publication Number US2016/0207954, A Non-Caloric Sweetener) via a fermentation pathway with modified microbes. Alternatively, other non-biologic synthetic means can be used to develop steviol glycosides of interest.

From a biological perspective, all steviol glycosides are formed by a series of glycosylation reactions of steviol, which typically are catalyzed by UDP-glycosyltransferase (UGT) enzymes using uridine 5'-diphosphoglucose (UDP-glucose) as a donor of the sugar moiety. In plants, UGTs are a very divergent group of enzymes that transfer a glucose residue from UDP-glucose to steviol. In these reactions stevioside is often an intermediate in the biosynthesis of various rebaudioside compounds. For example, glycosylation of stevioside at the C-3' at the C-13-O-glucose of stevioside yields rebaudioside A; while glycosylation at the C-2' at the 19-0-glucose position of stevioside yields rebaudioside E.

According to the current disclosure, a practical approach to improve the taste quality of *stevia* extracts is to increase the yield of those rebaudioside compounds that have more desirable taste characteristics in general and to do this via a more productive synthetic pathway and associated processes. Of those steviol glycosides tested many believe that Reb M has the most desirable taste and chemical characteristics for use in food and beverages. As stated above, however, the plant has vanishingly small amounts of this compound present in its leaves and therefore an alternative processes is needed to enable and assist in the large-scale production of this glycoside as well as to provide alternate sweeteners to the food and beverage industry.

Accordingly, there is a need for steviol glycosides with better and more consistent taste profiles to be developed as commercial products and for such steviol glycosides to utilize a relative common starting substrate, such as more abundant steviol glycosides as starting molecule, so that such production of desirable glycosides can be commercially as cost effective as possible. The present disclosure provides a method of enhancing the production of the desired steviol glycosides.

New production methods are also needed to reduce costs of steviol glycoside production and lessen the environmental impact of large scale cultivation and processing (Yao et al., 1994). One such potential solution is the use of fermentation bio-conversion technology that allows the production in certain microbial species or other recombinant cells that increases the selectivity, abundance and purity of desired steviol glycosides available for commerce and enhancing the presence of a desired rebaudioside using a hydrolytic enzyme to drive such production in cellular lysate from modified microbial cultures or other modified cell cultures.

SUMMARY OF THE INVENTION

The present disclosure encompasses, in part, a method of producing enhanced amounts of rebaudioside M (Reb M) from various steviol glycosides utilizing the hydrolytic activity of beta-glucosidase. More specifically, the present disclosure provides an improved process to produce desired steviol glycosides from disrupted recombinant cells (e.g., recombinant microbial cells) containing substrates of interest. This is where such cells (e.g., microbes) have been modified to carry genes capable of generating steviol glycosides of interest including rebaudioside A (Reb A), rebaudioside E (Reb E) and/or stevioside. In this embodiment, the process comprises the steps of obtaining the material from disrupted cells (e.g., microbial cells) and carrying out enzymatic hydrolysis on the steviosides present in said waste product to enhance the production of Reb M.

In terms of product/commercial utility there are several dozen products containing steviol glycosides on the market in the United States and can be used in everything from analgesics to pest repellents as well as in foods and as in dietary supplements. Products containing steviol glycosides of interest can include aerosols, liquids, or granular formulations.

As for the cellular system of the current disclosure, it is selected from the group consisting of bacteria, yeast, and a combination thereof, or any cellular system that would allow the genetic transformation with the selected genes and thereafter the biosynthetic production of the desired steviol glycosides from steviol. In a most preferred microbial system, *E. coli* are used to produce the desired steviol glycoside compounds later exposed to beta-glucosidase hydrolysis.

Beta-glucosidases are constitutive enzymes often present in the lower gastrointestinal tracts of animals and are useful as an aid in digestion and absorption of food material. According to the current disclosure B-glu1 is used to hydrolyze stevioside, rebaudioside E (Reb E), rebaudioside A (Reb A), rebaudioside I (Reb I), rebaudioside D (Reb D), rebaudioside G (Reb G) and rubusoside. Hydrolysis proceeds via initial formation of steviolbioside with steviol as the final product of hydrolysis.

Accordingly, aspects of the disclosure provide methods of altering the glycosylation of a steviol glycoside comprising a) providing a recombinant cell (e.g., a microbe, alga or plant cell) modified to produce a first substrate; b) disrupting said recombinant cell to release its cellular cytosol where such cytosol contains said first substrate; c) obtaining the cytosol from said recombinant cell; d) exposing said cytosol to a beta-glucosidase where such beta-glucosidase has hydrolytic activity for sufficient time to generate a second substrate of interest through the removal of at least one glucosyl group from said first substrate; and, e) collecting said second substrate of interest.

In some embodiments, said first substrate is a steviol glycoside. In some embodiments, said second substrate of interest is Reb M. In some embodiments, said second substrate of interest is Reb B. In some embodiments, said second substrate of interest is Reb A. In some embodiments, the first and second substrate are those described in Table 1 or in a Figure herein (e.g., FIG. 9).

In some embodiments, said hydrolytic activity functions to remove a glucosyl group from the C19 position of said steviol glycoside. In some embodiments, said hydrolytic activity functions to remove a glucosyl group from the C13 position of said steviol glycoside. In some embodiments, said hydrolytic activity functions to remove a glucosyl group from either the C19 position of said steviol glycoside or the C13 position of said steviol glycoside. In some embodiments, said hydrolytic activity functions to remove a glucosyl group from both the C19 position of said steviol glycoside and the C13 position of said substrate.

In some embodiments, said hydrolytic activity functions to remove a glucosyl group from the C19 position of rubusoside to produce steviol-13-gluoside. In some embodiments, said hydrolytic activity functions to remove a glucosyl group from the C19 position of stevioside to produce steviolbioside. In some embodiments, said hydrolytic activity functions to remove a glucosyl group from the C19 position of Reb E to produce steviolbioside. In some embodiments, said hydrolytic activity functions to remove a glucosyl group from the C19 position of Reb I to produce Reb A. In some embodiments, said hydrolytic activity functions to remove a glucosyl group from the C19 position of Reb A to produce Reb B.

In some embodiments, said hydrolytic activity functions to remove a glucosyl group from the C13 position of steviol-13-gluoside to produce steviol. In some embodiments, said hydrolytic activity functions to remove a glucosyl group from the C13 position of Reb D to produce Reb B or Reb A. In some embodiments, said hydrolytic activity functions to remove a glucosyl group from the C19 position and from the C13 position of Reb G to produce steviol-13-glucoside.

Methods provided herein, in some aspects, further comprise the use of beta-galactosidase or pectinase enzymes to increase the speed of enzymatic hydrolysis. In some embodiments, methods provided herein further comprise expressing a steviol glycoside in a transformed cellular system; growing the cellular system in a medium; and, producing said second substrate of interest.

In some embodiments, said time period for beta-glucosidase exposure to said first substrate is at least 6 hours.

In some embodiments, said time period for beta-glucosidase exposure to said first substrate is at least 12 hours. In some embodiments, said time period for beta-glucosidase exposure to said first substrate is at least 18 hours. In some embodiments, said time period for beta-glucosidase exposure to said first substrate is at least 24 hours. In some embodiments, said second substrate of interest is a steviol glycoside.

In some embodiments, the beta-glucosidase has an amino acid sequence that has at least 90% (e.g., at least 90%, at least 91%, at least 92%, at least 93%, at least 94%, at least 95%, at least 96%, at least 97%, at least 98%, at least 99%, or 100%) identity to SEQ ID NO:1. In some embodiments, the beta-glucosidase has an amino acid sequence that is at least 95% (e.g., at least 95%, at least 96%, at least 97%, at least 98%, at least 99%, or 100%) identical to SEQ ID NO:3.

In some embodiments, the recombinant cell is selected from the group consisting of: a bacterium, a yeast, a filamentous fungus, a cyanobacteria alga and a plant cell. In some embodiments, the recombinant cell (e.g., microbe) is selected from the group consisting of: *Escherichia*; *Salmonella*; *Bacillus*; *Acinetobacter*; *Streptomyces*; *Corynebacterium*; *Methylosinus*; *Methylomonas*; *Rhodococcus*; *Pseudomonas*; *Rhodobacter*; *Synechocystis*; *Saccharomyces*; *Zygosaccharomyces*; *Kluyveromyces*; *Candida*; *Hansenula*; *Debaryomyces*; *Mucor*; *Pichia*; *Torulopsis*; *Aspergillus*; *Arthrobotlys*; *Brevibacteria*; *Microbacterium*; *Arthrobacter*; *Citrobacter*; *Escherichia*; *Yarrowia*; *Klebsiella*; *Pantoea*; *Salmonella Corynebacterium*; *Clostridium*; and, *Clostridium acetobutylicum*.

In some embodiments, said second substrate of interest is a steviol glycoside. In some embodiments, the second substrate of interest is Reb E. In some embodiments, said second substrate is a mixture of Reb E, Reb D4 and Reb M. In some embodiments, the second substrate of interest is Reb D4. In some embodiments, said second substrate of interest is a steviol glycoside mixture and the steviol glycoside content of this mixture combined is greater than any other components of the cytosol derived concentrate by weight on a dry basis.

In some embodiments, the second substrate of interest in step e) is a crude product and step e) further comprises i) purifying said crude product; and, ii) removing solvents under vacuum to provide a concentrated product.

In some embodiments, said crude product is purified by column chromatography. In some embodiments, said crude product is purified by acid-base extraction. In some embodiments, said crude product is purified by vacuum distillation.

Methods provided herein, in some embodiments, further comprise purifying the concentrated product using a semi-preparative HPLC.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

FIG. 1A: HPLC profiles of the rubusoside hydrolysis products. a: standard of steviol ("S"); b: standard of rubusoside ("Rub"); c-d: Rubusoside was cleaved by recombinant B-glu1 enzyme at 1 hour (c) and 3 hours (d); e-f: Rubusoside was hydrolyzed by disrupted *Pichia* cells at 1 hour (e) and 6 hours (f). FIG. 1B: Rubusoside hydrolysis pathway catalyzed by B-glu1. Rubusoside was hydrolyzed by recombinant B-glu1 enzyme and disrupted *Pichia* cells to produce steviol-13-glucoside ("S-13-G") and steviol.

FIG. 2A: HPLC profiles of the stevioside hydrolysis products. a: standard of stevioside ("ST"); b: standard of steviolbioside ("SB"); c-e: Stevioside was hydrolyzed by recombinant B-glu1 enzyme at 1 hour (c), 6 hours (d) and 24 hours (e). FIG. 2B: Stevioside hydrolysis pathway catalyzed by B-glu1. Stevioside is hydrolyzed by recombinant B-glu1 enzyme and disrupted *pichia* cells to produce steviolbioside.

FIG. 3A: HPLC profiles of the rebaudioside E hydrolysis products. a: standard of steviolbioside ("SB"); b: standard of rebaudioside E ("E"); c-e: Rebaudioside E was hydrolyzed by recombinant B-glu1 enzyme at 1 hour (c), 6 hours (d) and 24 hours (e). FIG. 3B: Rebaudioside E hydrolysis pathway catalyzed by B-glu1. Rebaudioside E is hydrolyzed by recombinant B-glu1 enzyme and disrupted *pichia* cells to produce steviolbioside.

FIG. 4A: HPLC profiles of the rebaudioside A hydrolysis products. a: standard of rebaudioside A ("Reb A"); b: standard of rebaudioside B ("Reb B"); c-d: Rebaudioside A was hydrolyzed by recombinant B-glu1 enzyme at 1 hour (c) and 6 hours (d). FIG. 4B: Rebaudioside A hydrolysis pathway catalyzed by B-glu1. Rebaudioside A is hydrolyzed by recombinant B-glu1 enzyme and disrupted *pichia* cells to produce Rebaudioside B.

FIG. 5A: HPLC profiles of the rebaudioside I hydrolysis products. a: standard of rebaudioside A ("Reb A"); b: standard of rebaudioside B ("Reb B"); c: standard of rebaudioside I ("Reb I"). d-f: Rebaudioside I was hydrolyzed by recombinant B-glu1 enzyme at 1 hour (d), 6 hours (e) and 24 hours (f). FIG. 5B: Rebaudioside I hydrolysis pathway catalyzed by B-glu1. Rebaudioside I is hydrolyzed by recombinant B-glu1 enzyme to produce rebaudioside A and rebaudioside B.

FIG. 6A: HPLC profiles of the rebaudioside D hydrolysis products. a: standard of rebaudioside B ("Reb B"); b: standard of rebaudioside D ("Reb D"); c-e: Rebaudioside D was hydrolyzed by recombinant B-glu1 enzyme at 1 hour (c), 6 hours (d) and 24 hours (e). FIG. 6B: Rebaudioside D hydrolysis pathway catalyzed by B-glu1. Rebaudioside D is hydrolyzed by recombinant B-glu1 enzyme to produce rebaudioside A and rebaudioside B.

FIG. 7A: HPLC profiles of the rebaudioside G hydrolysis products. a: standard of steviol ("Steviol"), steviol-13-glucoside ("S-13-G"); b: standard of rebaudioside G ("G"); b-d: Rebaudioside G was hydrolyzed by recombinant B-glu1 enzyme at 0.5 hour (c), 1 hour (d) and 6 hours (e); f: Rebaudioside G was hydrolyzed by disrupted *pichia* cells at 24 hours (f). FIG. 7B: Rebaudioside G hydrolysis pathway catalyzed by B-glu1. Rebaudioside G was hydrolyzed by recombinant B-glu1 enzyme and disrupted *pichia* cells to produce steviol-13-glucoside ("S-13-G") and steviol.

DETAILED DESCRIPTION

Explanation of Terms Used Herein

Figure 1A:
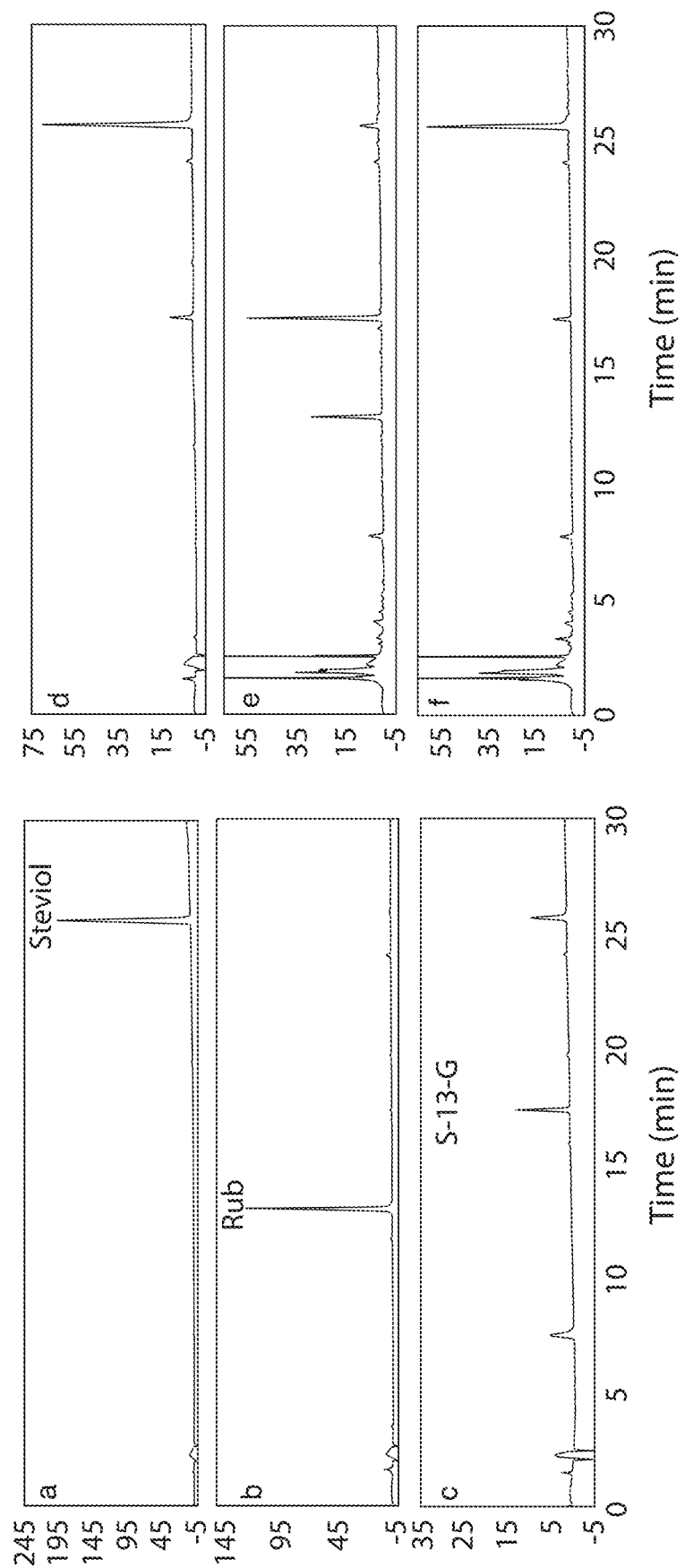
FIGS. 1A-1B show that rubusoside is hydrolyzed by B-glu1 enzyme and disrupted *Pichia* cells.

Steviol Glycosides are a class of chemical compounds responsible for the sweet taste of the leaves of the South American plant *Stevia rebaudiana* (Asteraceae), and can be used as sweeteners in food, feed and beverages.

Definitions

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Coding sequence is to be given its ordinary and customary meaning to a person of ordinary skill in the art, and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current disclosure a yeast as claimed herein are eukaryotic, single-celled microorganisms classified as members of the fungus kingdom. Yeasts are unicellular organisms which evolved from multicellular ancestors but with some species useful for the current disclosure being those that have the ability to develop multicellular characteristics by forming strings of connected budding cells known as pseudohyphae or false hyphae.

The names of the UGT enzymes used in the present disclosure for the production of various steviol glycosides are consistent with the nomenclature system adopted by the UGT Nomenclature Committee (Mackenzie et al., "*The UDP glycosyltransferase gene super family: recommended nomenclature updated based on evolutionary divergence*," PHARMACOGENETICS, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number 1.

Structural Terms

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxy inosine residues. A nucleic acid sequence and all of its degenerate variants will express the same amino acid or polypeptide.

The terms "polypeptide," "protein," and "peptide" are to be given their respective ordinary' and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of original Y skill in the aft, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

"Transformation cassette" refers to a specific vector containing a foreign gene and having elements in addition to the foreign gene that facilitate transformation of a particular host cell.

"Expression cassette" refers to a specific vector containing a foreign gene and having elements in addition to the foreign gene that allow for enhanced expression of that gene in a foreign host.

The present disclosure relates to the production of a steviol glycoside of interest by B-glu1 enzyme.

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by Greene Publishing and Wiley-Interscience, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family of GT enzymes, also known as the UDP glycosyltransferases (UGTs), transfer UDP-activated sugar moieties to specific acceptor molecules. These are the molecules that transfer such sugar moieties in the steviol glycosides to create various rebaudiosides. Each of these UGTs have their own activity profile and preferred structure locations where they transfer their activated sugar moieties.

Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

A number of molecular biology techniques have been developed to operably link DNA to vectors via complementary cohesive termini. In one embodiment, complementary homo-polymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference to the extent it is consistent herewith).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared by the use of PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into a recombinant host cell (e.g., plant or microbial host cells) by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a petunia plant cell.

Microbial host cell and other host cell expression systems and expression vectors containing regulatory sequences that direct high-level expression of foreign proteins is well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells and other host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell or other host cell are numerous and familiar to those skilled in the art. Virtually any promoter capable of driving these genes is suitable for the subject technology including but not limited to CYCI, HIS3, GALI, GALIO, ADHI, PGK, PH05, GAPDH, ADCI, TRPI, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns in order to facilitate polynucleotide expression.

For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (ss) of the ribulose-1,5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll alb binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Cell Disruption Techniques

Cell disruption is a collection of techniques used for releasing biomolecules of interest from inside the cell. Many biotechnologically produced compounds are intracellular and must be released from cells before recovery. The efficient recovery of products requires cell disruption, which can be achieved by using different methods and technologies, either mechanical or non-mechanical methods depending upon the biomolecule of interest and the cellular system being used. It should be noted that all disruption methods will release molecules of interest, here steviol glycosides, and other molecules that can cause the breakdown of proteins of interest within the lysate. Considerations need to be made to prevent this if protein activity is important to the downstream work. Lysing samples in highly denaturing solutions or high pH minimizes enzymatic activity. Performing the disruption on ice or lower temperatures will also help minimize degradation of samples. Thus, one technique to inhibit protease activity is to have a general phosphatase inhibitor cocktail available for the lysate once disrupted.

Known Disruption Techniques that can be Used According to the Current Disclosure Standard disruption consists of mechanical homogenization, French press, sonication, bead homogenization, grinding, freeze-thaw lysis, detergent lysis, enzymatic lysis and osmotic lysis.

Mechanical homogenization includes using a hand-held device, like a Dounce homogenizer, or something like a blender to homogenize the tissue. This method is useful for non-seed plant type material or soft tissues (i.e. Liver tissue.) French press uses shear force to homogenize the tissue. An example of this would be taking a cell suspension and forcing it through a narrow gauge syringe using a syringe barrel and plunger. This works well with bacteria, yeast, fungi, algae and mammalian cell culture but is difficult to scale-up.

Sonication uses short bursts of ultrasonic waves to disrupt the tissue. This method generates a lot of heat and will typically have to be performed on ice to maintain the protein. This method is also effective for bacteria, yeast, fungi, algae and mammalian cell culture and is the preferred method for the current disclosure.

Bead homogenization involves using glass or metal beads to apply gentle abrasion while vortexing them with the tissue or cell suspension. Grinding involves using a mortar and pestle to homogenize the tissue sample. The most common method is to freeze and grind the sample using liquid nitrogen. Freeze-thaw lysis is pretty much as it sounds, using liquid nitrogen or a freezer to freeze the cells and then allow them to thaw. When cells are frozen the water inside the cells expands as it freezes causing the cells to burst open. This method is effective for mammalian cells.

Enzymatic lysis consists of suspending the cells in iso-osmotic buffers containing enzymes that can digest the cell wall (i.e. Zymolyase for yeast cells). This lysis method is often used in conjunction with another disruption technique (usually sonication) to ensure complete lysis of the sample. This technique is effective with bacteria, yeast, fungi, algae, non-seed plant material and mammalian cell culture and is a technique that is also embodied in the current disclosure.

Detergent lysis involves suspending the cells in a detergent solution to solubilize the cell membrane, releasing the cell contents. This method also generally uses another lysis method, such as sonication to ensure complete lysis. This method is effective with mammalian cell culture.

Osmotic lysis involves suspending cells in hypotonic (low salt) solution. This causes the cells to swell and eventually burst releasing the contents of the cells for further use.

Typically, in the in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

Typically, the reaction temperature of the in vitro method is from about 20° C. to about 40° C., suitably from 25° C. to about 37° C., more suitably from 28° C. to about 32° C.

One with skill in the art will recognize that the steviol glycoside composition produced by the method described herein can be further purified and mixed with other steviol glycosides, flavors, or sweeteners to obtain a desired flavor or sweetener composition. For example, a composition enriched with rebaudioside D4 or rebaudioside M produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside D4 or rebaudioside M) obtained from the steviol glycoside composition described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside composition described herein (including rebaudioside D, rebaudioside E, rebaudioside D4, rebaudioside M or a combination thereof) can be included in food products (such as beverages, soft drinks, ice cream, dairy products, confectioneries, cereals, chewing gum, baked goods, etc.), dietary supplements, medical nutrition, as well as pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the beta-glucosidase genes of the current disclosure are capable of directing the production of a variety of steviol glycosides and have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

According to the current disclosure beta-glucosidase ("B-glu1") can be used to hydrolyze steviol glycosides and reduce the production of unwanted steviol glycosides in a novel way. The presence of undesirable steviol glycosides in stevia extract or fermentation productions affect the overall taste profile and usefulness of steviol glycosides. By reducing production steps the current disclosure will reduce both the cost of purification and the production of desired steviol glycosides in stevia crude extract.

The disclosure will be more fully understood upon consideration of the following non-limiting Examples. It should be understood that the Examples below, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Example 1: Identification of Beta-Glycosidase in Pichia pastoris

According to the current disclosure Pichia pastoris genome analysis was completed and several beta-glycosidase candidate genes were identified. Full length DNA fragments of all candidate beta-glucosidase genes were commercially synthesized. Almost all codons of the cDNA were changed to those preferred for E. coli (Genscript, NJ). The synthesized DNA was cloned into a bacterial expression vector pETite N-His SUMO Kan Vector (Lucigen). These same experiments could be performed in Yarrowia lipolytica with sequences optimized for such use.

Each expression construct was transformed into E. coli BL21 (DE3), which was subsequently grown in LB media containing 50 µg/mL kanamycin at 37° C. until reaching an OD600 of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 ug/ml lysozyme, 5 ug/ml DNase I, 20 mM imidazole, 500 mM NaCl, 10% glycerol, and 0.4% Triton X-100). The cells were disrupted by sonication under 4° C., and the cell debris was clarified by centrifugation (18,000×g; 30 min). Supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged beta-glucosidase recombinant polypeptides were eluted by equilibration buffer containing 250 mM imidazole.

The purified candidate beta-glucosidase recombinant polypeptides were assayed for de-glycosylation activity by using various steviol glycosides as substrate. Typically, the recombinant polypeptide (10 µg) was tested in a 300 µl in vitro reaction system. The reaction system contains 50 mM potassium phosphate buffer, pH 7.2, 1 mg/ml steviol glycoside. The reaction was performed at 30-37° C. and 50 ul reaction was terminated by adding 200 µL 1-butanol at various time points. The samples were extracted three times with 200 µL 1-butanol. The pooled fraction was dried and dissolved in 100 µL 80% methanol for high-performance liquid chromatography (HPLC) analysis.

Pichia cells were suspended in extraction buffer (50 mM potassium phosphate buffer, pH 7.2; 150 mM NaCl). After sonication, the supernatant (crude extract) was collected by centrifuge set at 12,000 g at 4° C. The resulting crude protein (50 ug) was tested in a 300 ul in vitro reaction system. The reaction system contains 50 mM potassium phosphate buffer, pH 7.2, 1 mg/ml steviol glycoside. The reaction was performed at 30-37° C. and 50 ul reaction was terminated by adding 200 µL 1-butanol at various time points. The samples were extracted three times with 200 µL 1-butanol. The pooled fraction was dried and dissolved in 100 µL 80% methanol for high-performance liquid chromatography (HPLC) analysis.

HPLC analysis was then performed using a Dionex UPLC ultimate 3000 system (Sunnyvale, Calif.), including a quaternary pump, a temperature controlled column compartment, an auto sampler and a UV absorbance detector. A Synergi Hydro-RP column (Phenomenex) with guard column was used for the characterization of steviol glycosides in the pooled samples. Acetonitrile in water was used mobile phase in the HPLC analysis. The detection wavelength used in the HPLC analysis was 210 nm. After activity screening, we found Beta-glucosidase (B-glu1, SEQ: 1) has strong activity to cleave related steviol glycosides and is therefore a useful tool in the production of steviol glycosides of interest.

Figure 1B:
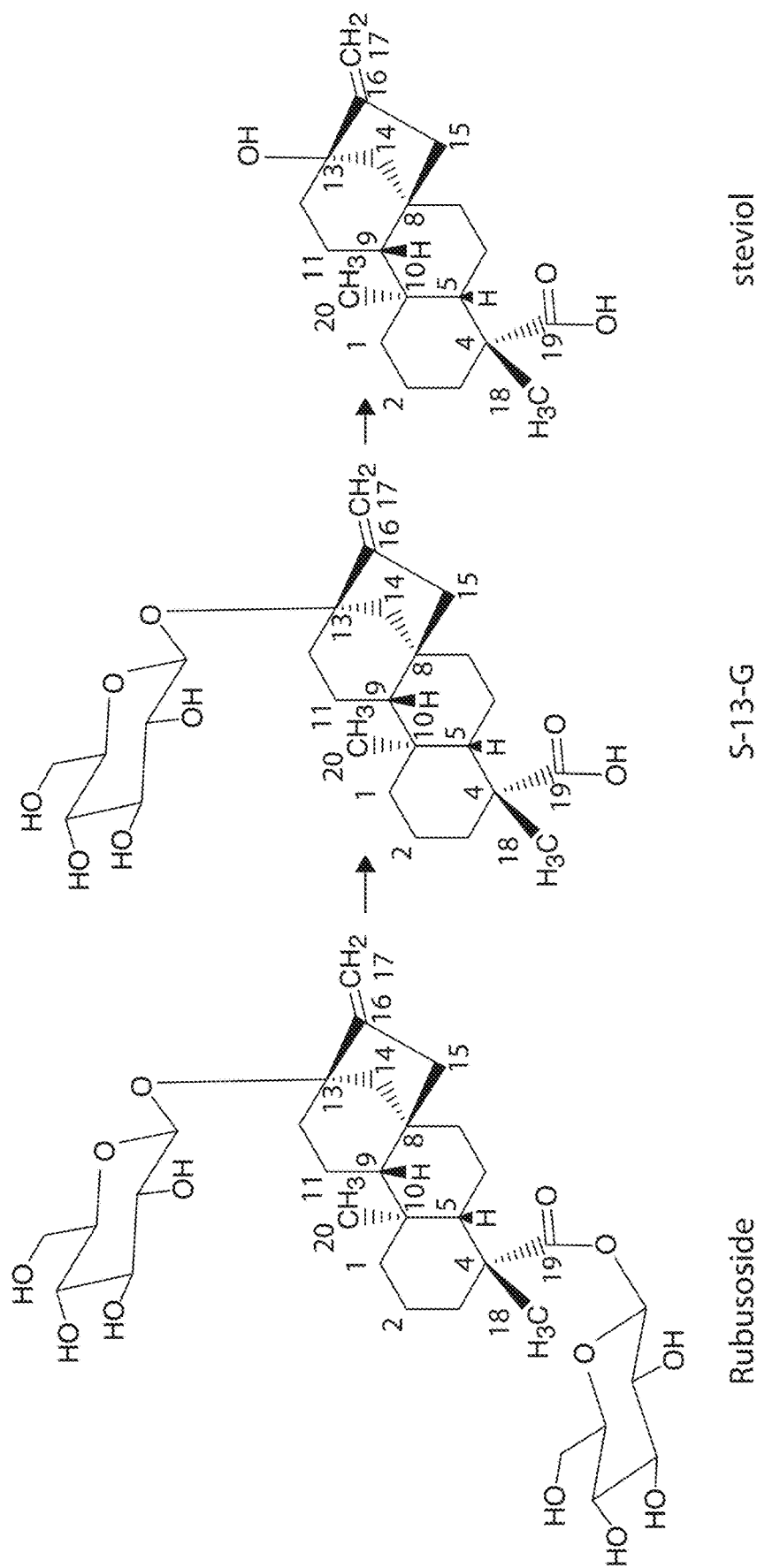

Example 2: Hydrolysis of Rubusoside by Use of the Recombinant B-glu1 and Disrupted Pichia Cells Rubusoside can be hydrolyzed by recombinant B-glu1 enzyme and disrupted Pichia cells to produce steviol-13-glucoside. The produced steviol-13-glucoside can be subsequently hydrolyzed to produce steviol (FIG. 1B). The reactions were setup as described in Example 1. 1 g/L rubusoside was added in the reaction as substrate. As shown in FIG. 1A, B-glu1 can remove a glucosyl group from C19 position of rubusoside to produce steviol-13-gluoside (FIG. 1A, panel c). The produced steviol-13-gluocside (S-13-G) will be converted to steviol at later time point (FIG. 1A, panel d). B-glu1 remove another glucosyl group from C13 position of steviol-13-glucoside. Since B-glu1 is an intercellular enzyme in Pichia cells, the disrupted Pichia cells release B-glu1 enzyme, which has same enzymatic activity to hydrolyze rubusoside to steviol-13-glucoside and continually to produce steviol (FIG. 1A, panels e and f).

Figure 2A:
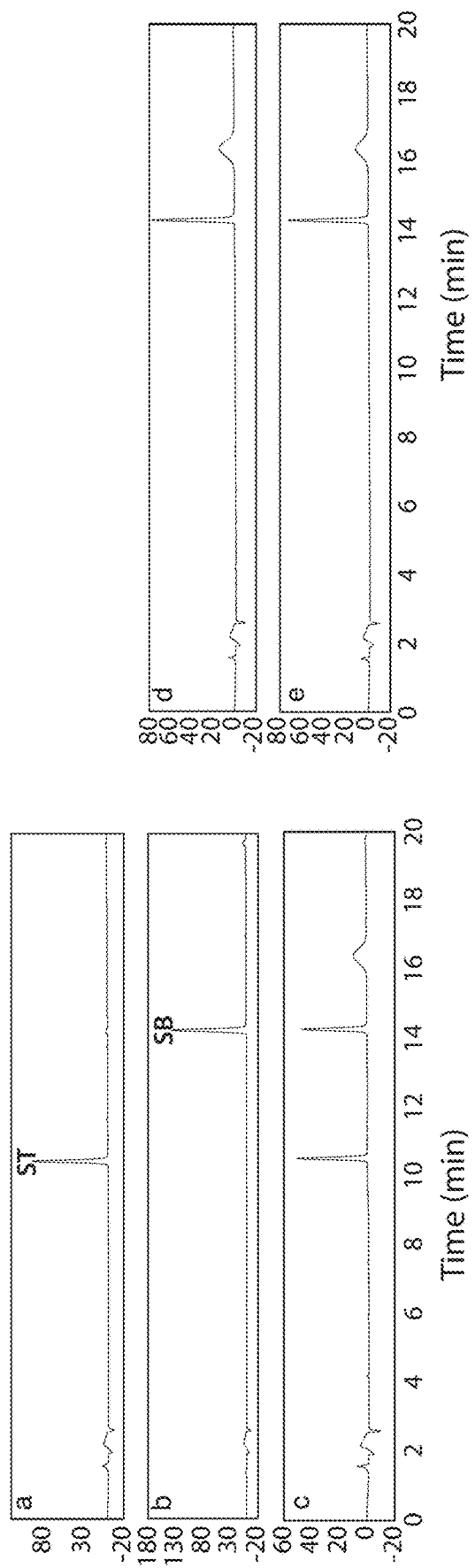
FIGS. 2A-2B show that stevioside is hydrolyzed by B-glu1 enzyme.
Figure 2B:
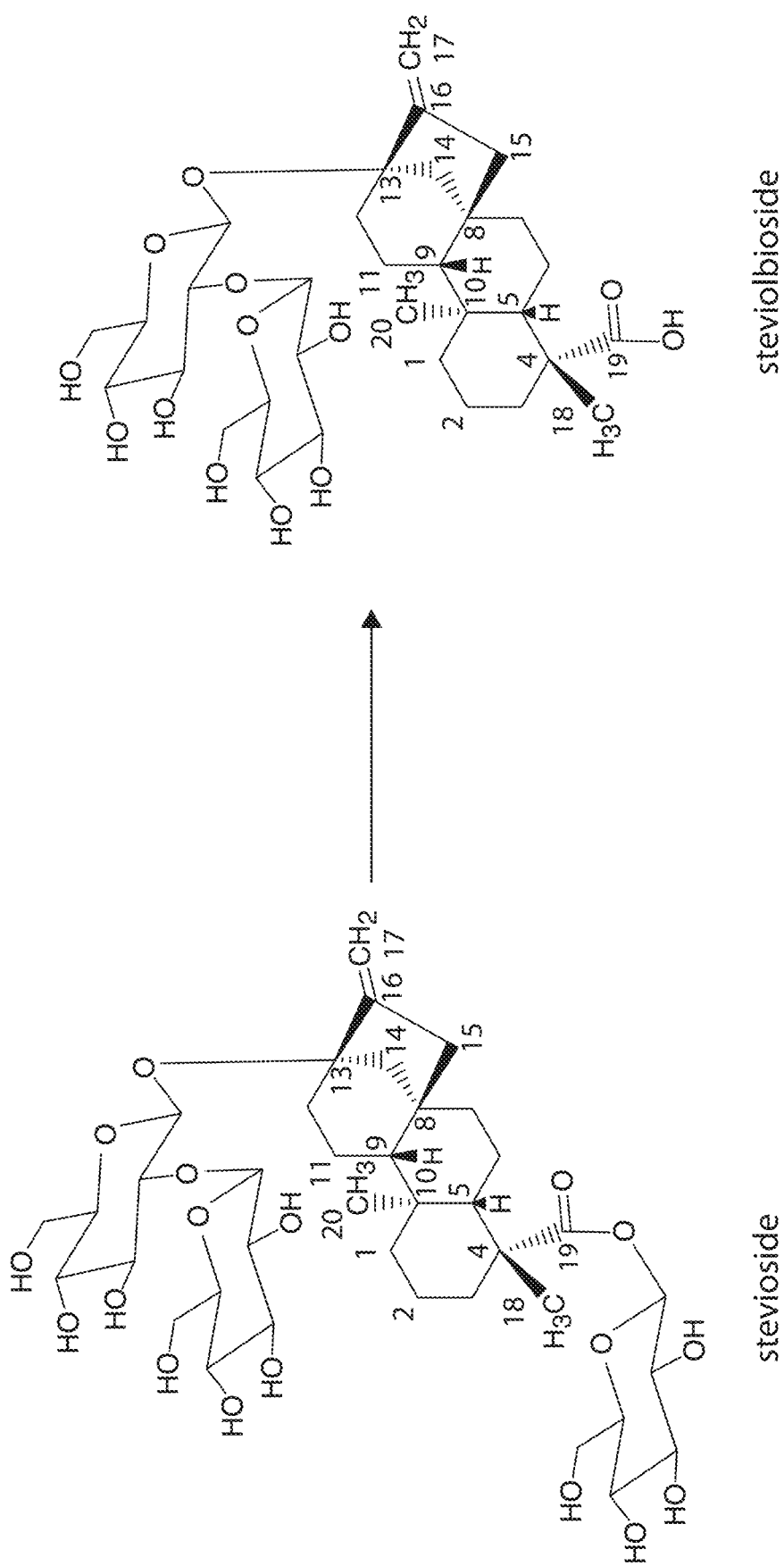
Figure 8:
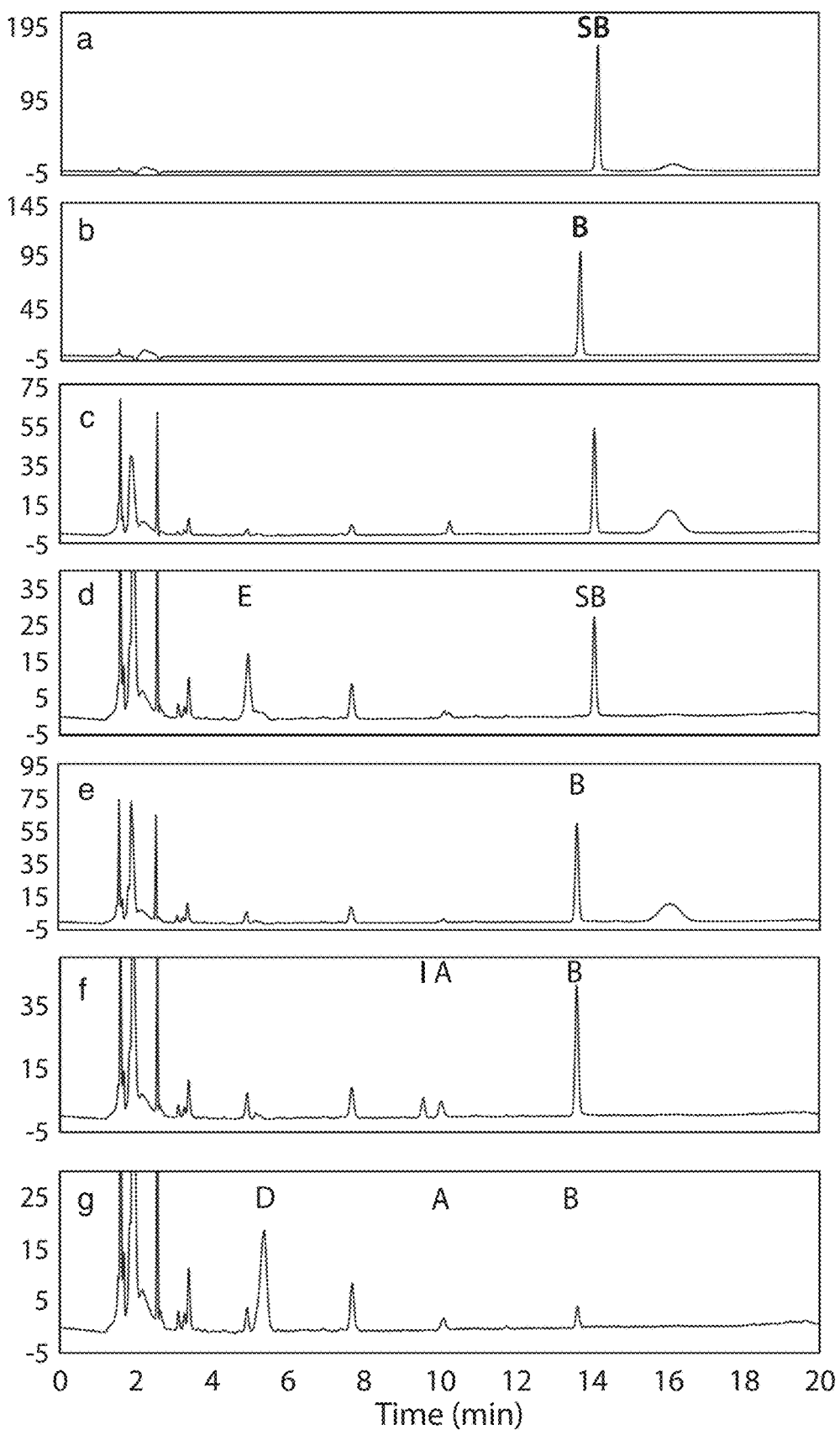
FIG. 8 shows that steviol glycosides are hydrolyzed by disrupted *pichia* cells. a: standard of steviolbioside ("SB"); b: standard of rebaudioside B ("B"); c: Stevioside was hydrolyzed by disrupted *pichia* cells at 24 hours; d: Rebaudioside E ("E") was hydrolyzed by disrupted *pichia* cells at 24 hours; e: Rebaudioside A ("A") was hydrolyzed by disrupted *pichia* cells at 24 hours; f: Rebaudioside I ("I") was hydrolyzed by disrupted *pichia* cells at 24 hours; g: Rebaudioside D ("D") was hydrolyzed by disrupted *pichia* cells at 24 hours.

Example 3: Hydrolysis of Stevioside by Use of the Recombinant B-glu1 and Disrupted Pichia Cells Stevioside can be hydrolyzed by recombinant B-glu1 enzyme and disrupted Pichia cells to produce steviolbioside (FIG. 2B). The reactions were setup as described in Example 1. 1 g/L stevioside was added in the reaction as substrate. As shown in FIGS. 2A-2B, B-glu1 can remove a glucosyl group from C19 position of stevioside to produce steviolbioside (FIG. 2A, panels c and d). Since B-glu1 is an intercellular enzyme in Pichia cells, the disrupted Pichia cells release B-glu1 enzyme, which has same enzymatic activity to hydrolyze stevioside to steviolbioside (FIG. 8, panel c).

Figure 3A:
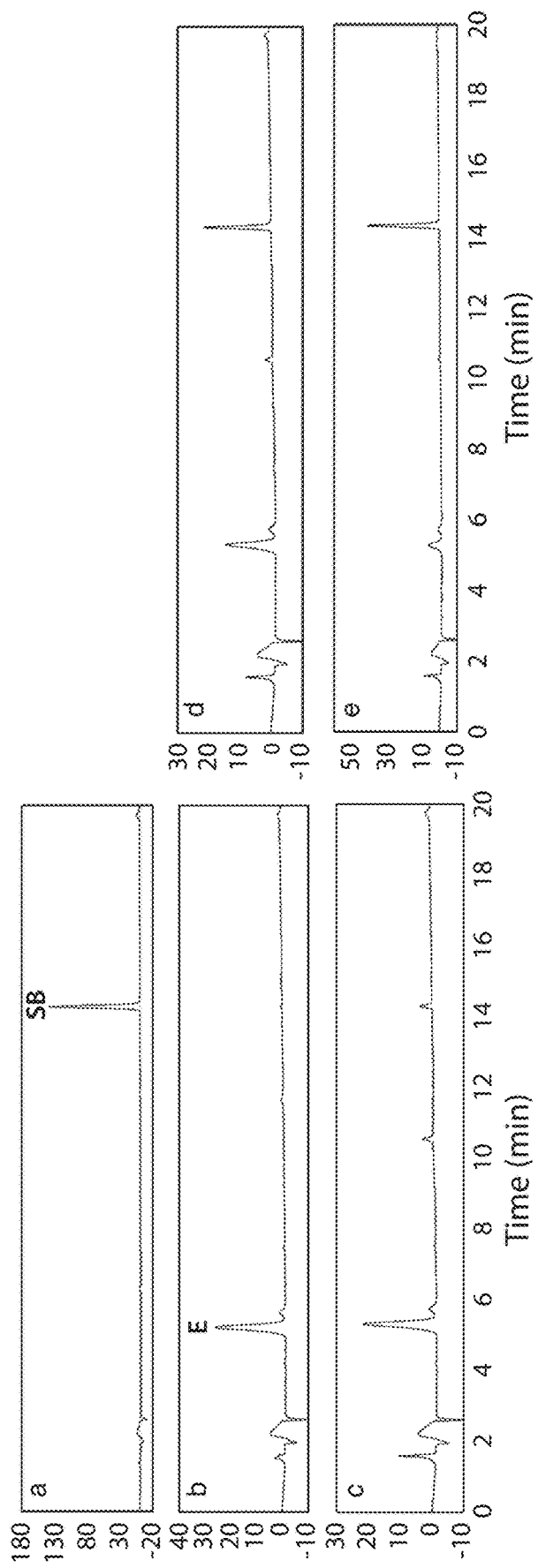
FIGS. 3A-3B show that rebaudioside E is hydrolyzed by B-glu1 enzyme.
Figure 3B:
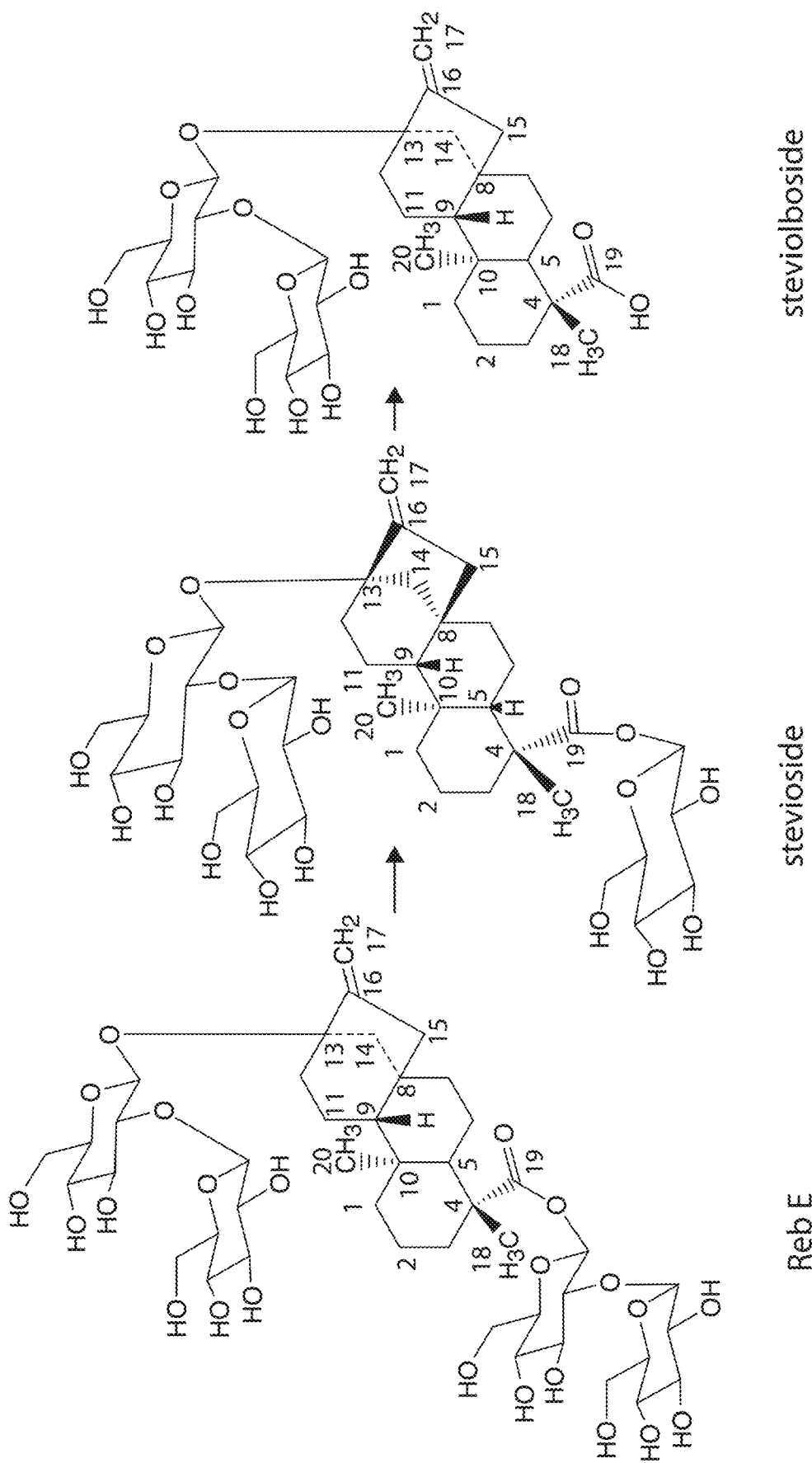

Example 4: Hydrolysis of Rebaudioside E by Use of the Recombinant B-glu1 and Disrupted Pichia Cells Rebaudioside E can be hydrolyzed by recombinant B-glu1 enzyme to produce steviolbioside (FIG. 3B). The reactions were setup as described in Example 1. 1 g/L rebaudioside E was added in the reaction as substrate. As shown in FIGS. 3A-3B, B-glu1 can remove the glucosyl group from C19 position of rebaudioside E to produce stevioside and steviolbioside (FIG. 3A, panels c-e). Since B-glu1 is an intercellular enzyme in Pichia cells, the disrupted Pichia cells release B-glu1 enzyme, which has same enzymatic activity to hydrolyze rebaudioside E to steviolbioside (FIG. 8, panel d).

Figure 4A:
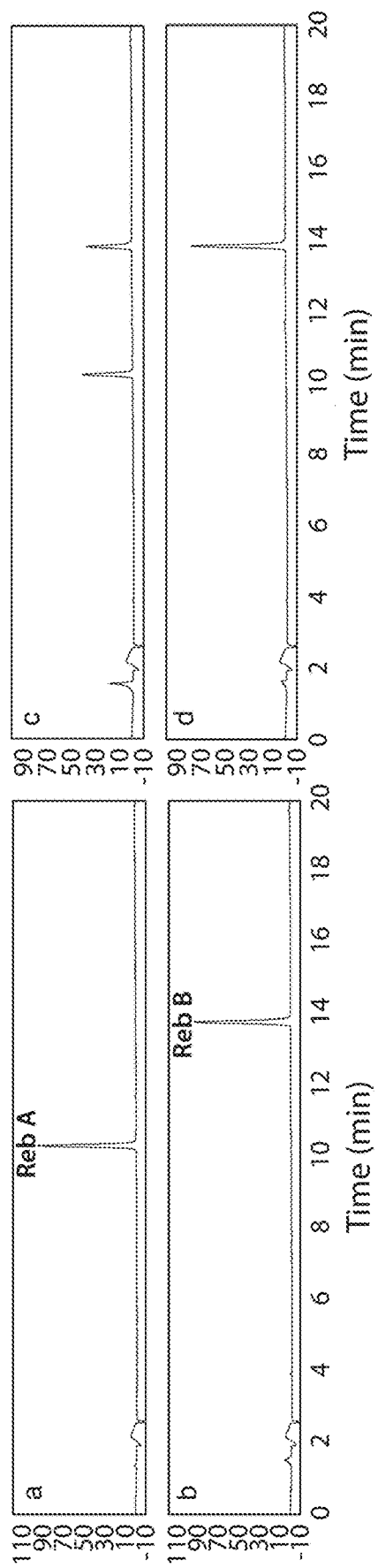
FIGS. 4A-4B show that rebaudioside A is hydrolyzed by B-glu1 enzyme.
Figure 4B:
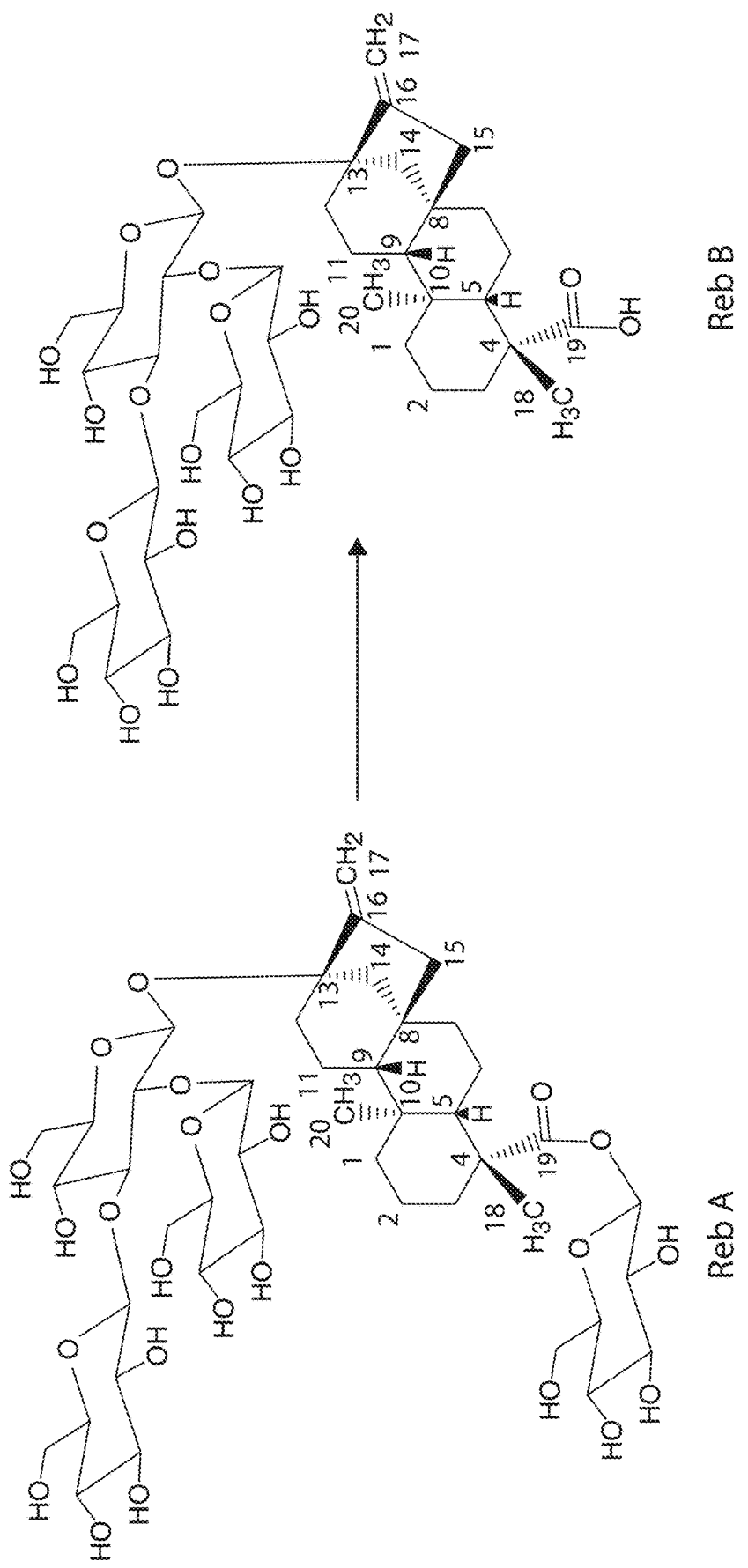

Example 5: Hydrolysis of Rebaudioside A by Use of the Recombinant B-glu1 and Disrupted Pichia Cells Rebaudioside A can be hydrolyzed by recombinant B-glu1 enzyme to produce rebaudioside B (FIG. 4B). The reactions were setup as described in Example 1. 1 g/L rebaudioside A was added in the reaction as substrate. As shown in FIGS. 4A-4B, B-glu1 can remove the glucosyl groups from C19 position of rebaudioside A to produce rebaudioside B (FIG. 4A, panels c-d). Since B-glu1 is an intercellular enzyme in Pichia cells, the disrupted Pichia cells release B-glu1 enzyme, which has same enzymatic activity to hydrolyze rebaudioside A to rebaudioside B (FIG. 8, panel e).

Figure 5A:
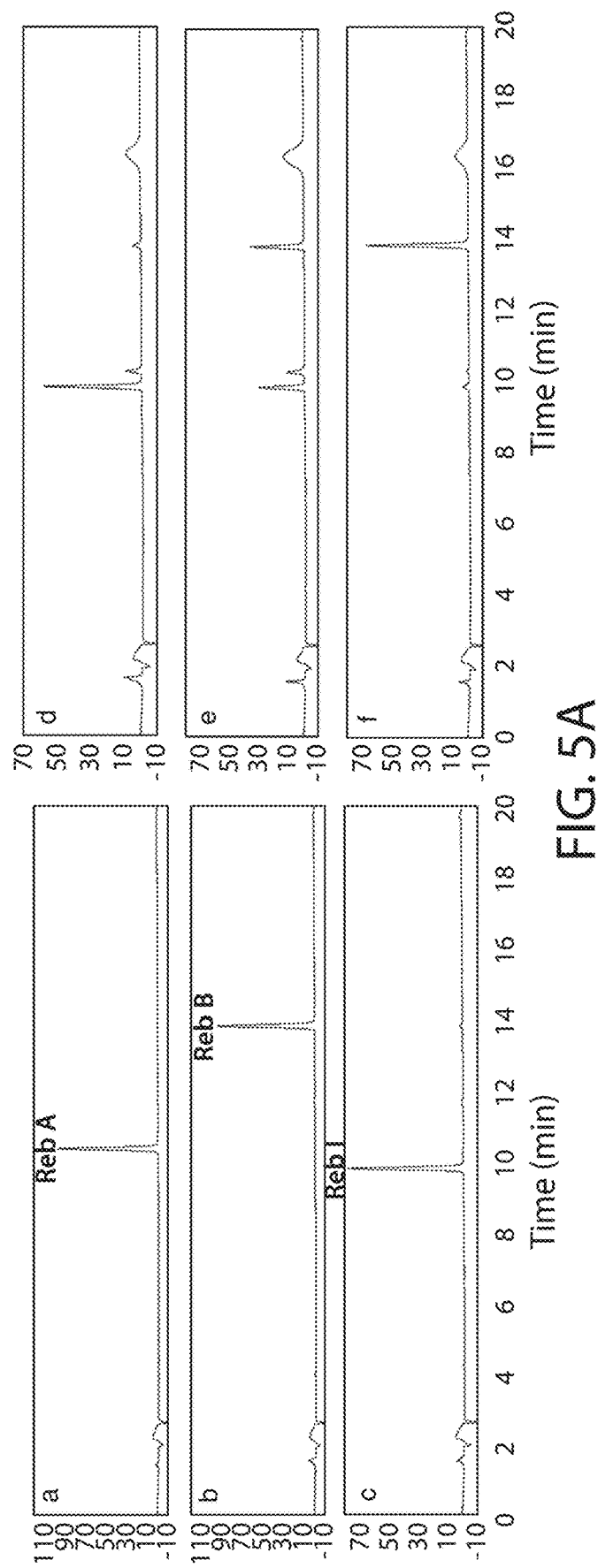
FIGS. 5A-5B show that rebaudioside I is hydrolyzed by B-glu1 enzyme.
Figure 5B:
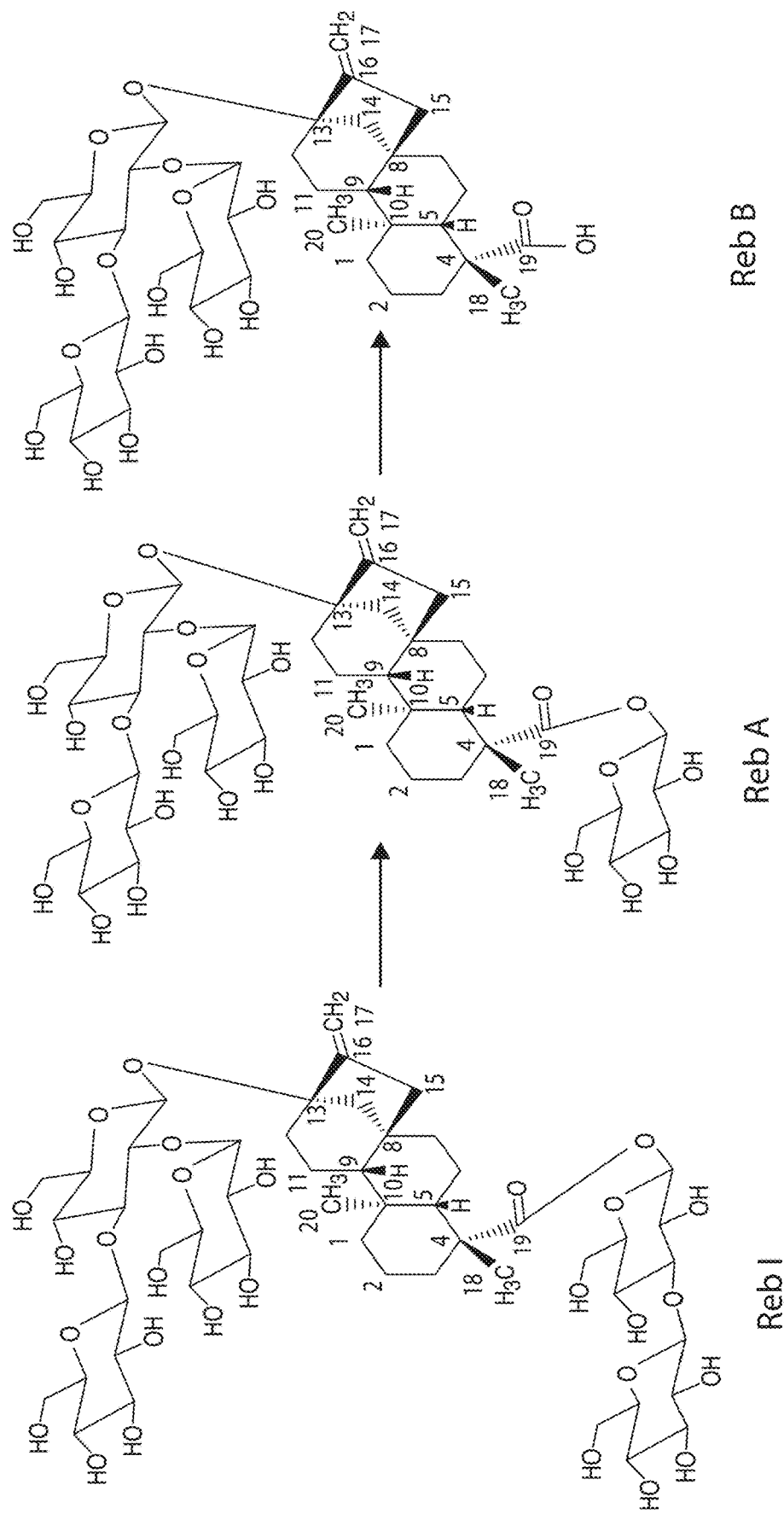

Example 6: Hydrolysis of Rebaudioside I by Use of the Recombinant B-glu1 and Disrupted Pichia Cells Rebaudioside I can be hydrolyzed by recombinant B-glu1 enzyme to produce rebaudioside A and the produced A can be hydrolyzed to produce rebaudioside B (FIG. 5B). The reactions were setup as described in Example 1. 1 g/L rebaudioside I was added in the reaction as substrate. As shown in FIGS. 5A-5B, B-glu1 can remove a glucosyl group from C19 position of rebaudioside I to produce rebaudioside A and subsequently remove another glucosyl group at C19 position of rebaudioside A to produce rebaudioside B (FIG. 5A, panels d-f). Rebaudioside I can be converted to rebaudioside A completely at 24 hrs (FIG. 5A, panel f). Since B-glu1 is an intercellular enzyme in Pichia cells, the disrupted Pichia cells release B-glu1 enzyme, which has same enzymatic activity to hydrolyze rebaudioside I to rebaudioside B (FIG. 8, panel f).

Figure 6A:
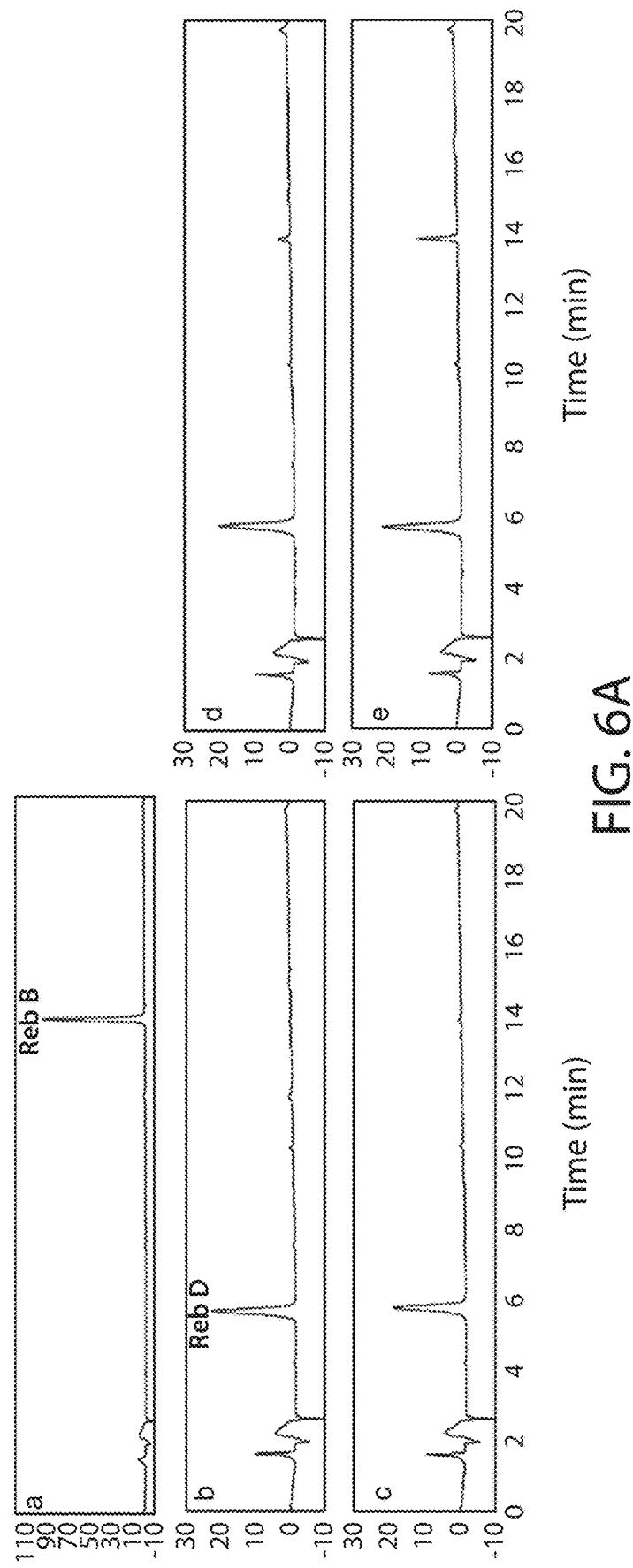
FIGS. 6A-6B show that rebaudioside D is hydrolyzed by B-glu1 enzyme.
Figure 6B:
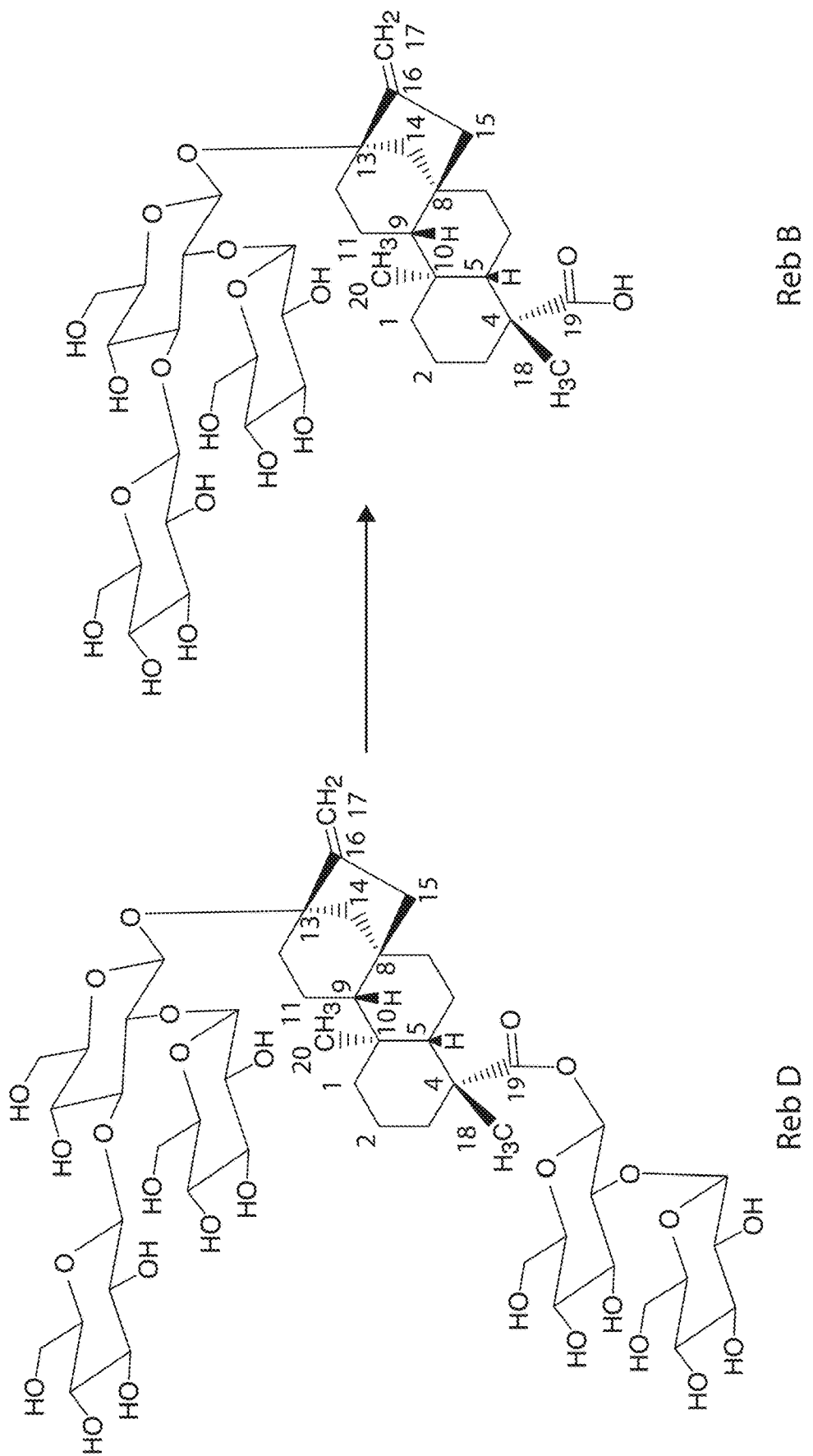

Example 7: Hydrolysis of Rebaudioside D by Use of the Recombinant B-glu1 and Disrupted Pichia Cells Rebaudioside D can be hydrolyzed by recombinant B-glu1 enzyme to produce rebaudioside B (FIG. 6B) and Reb A. The reactions were setup as described in Example 1. 1 g/L rebaudioside D was added in the reaction as substrate. As shown in FIGS. 6A-6B, B-glu1 can remove the glucosyl groups from C19 position of rebaudioside D to produce rebaudioside (FIG. 6A, panels c-e). Since B-glu1 is an intercellular enzyme in Pichia cells, the disrupted Pichia cells release B-glu1 enzyme, which has same enzymatic activity to hydrolyze rebaudioside D to rebaudioside B (FIG. 8, panel g).

Figure 7A:
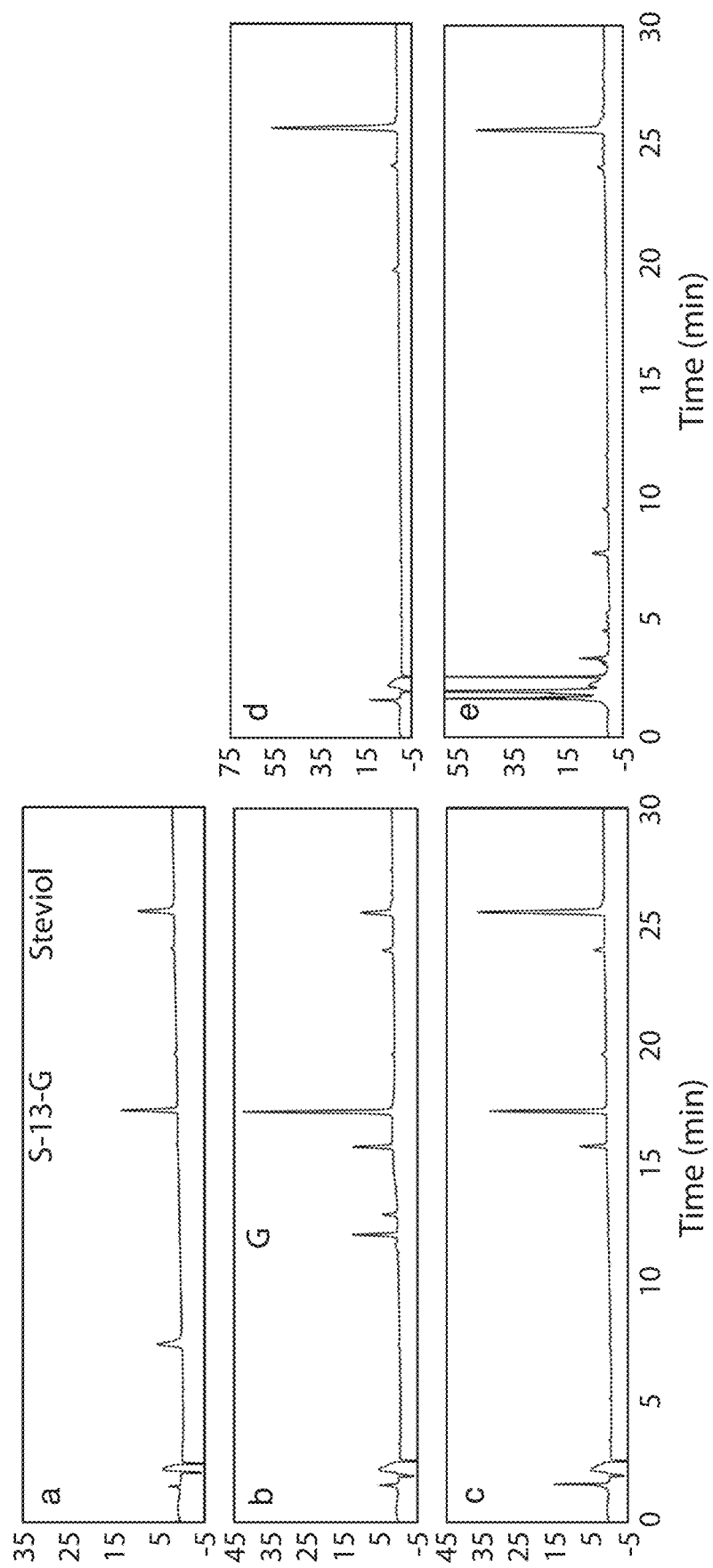
FIGS. 7A-7B show that rebaudioside G is hydrolyzed by B-glu1 enzyme and disrupted *pichia* cells.
Figure 7B:
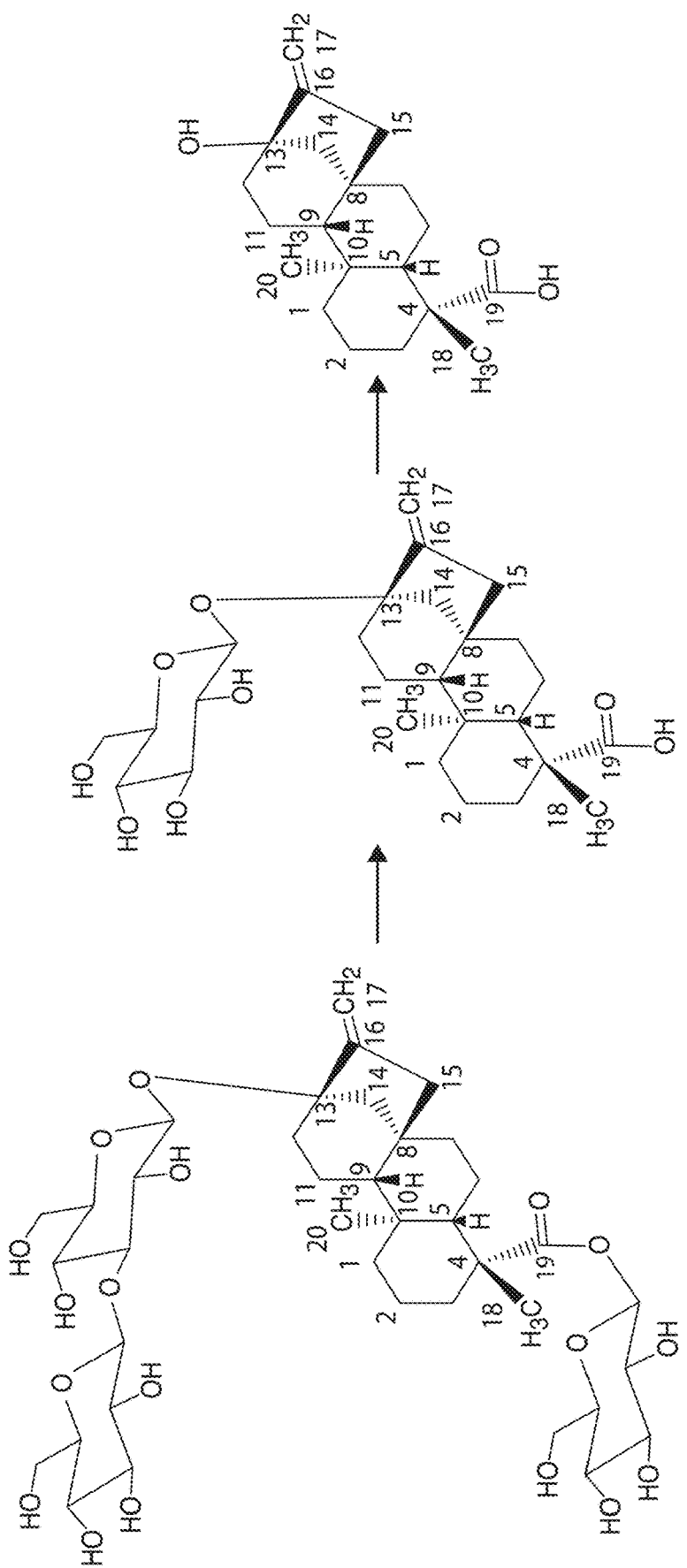

Example 8: Hydrolysis of Rebaudioside G by Use of the Recombinant B-glu1 and Disrupted Pichia Cells Rebaudioside G can be hydrolyzed by recombinant B-glu1 enzyme and disrupted Pichia cells to produce steviol-13-glucoside. The produced steviol-13-glucoside can be continually hydrolyzed to produce steviol (FIG. 7B). The reactions were setup as described in Example 1. 1 g/L rebaudioside G was added in the reaction as substrate. As shown in FIG. 7A, B-glu1 can remove the glucosyl groups from C13 and C19 position of rebaudioside G to produce steviol-13-gluoside (FIG. 7A, panels b-c). The produced steviol-13-gluocside (S-13-G) will be converted to steviol (FIG. 7A). The produced steviol-13-glucoside will be converted to steviol completely at 24 hrs (FIG. 7A, panel d). B-glu1 remove another glucosyl group from C13 position of steviol-13-glucoside. Since B-glu1 is an intercellular enzyme in Pichia cells, the disrupted Pichia cells release B-glu1 enzyme, which has same enzymatic activity to hydrolyze rebaudioside G to steviol-13-glucoside and continually to produce steviol (FIG. 7A, panel e).

According to the current disclosure we identified and quantified the enzymatic activity of beta-glucosidase on a Pichia pastoris cell lysate. This enzyme has specific activity that allows it to hydrolyze specific steviol glycosides (Table 1). Referring to FIGS. 7A-7B, Reb G is hydrolyzed by B-glu1 enzyme and disrupted Pichia cells. The HPLC shows the products of Reb G hydrolysis. In this effort steviol ("S"); steviol-13-glucoside ("S-13-G"); rubusoside ("Rub") were produced. The time course was a series of time points over 24 hours. Steviol-13-glucoside ("S-13-G") and steviol were produced by recombinant Pichia pastoris cultures.

Figure 9:
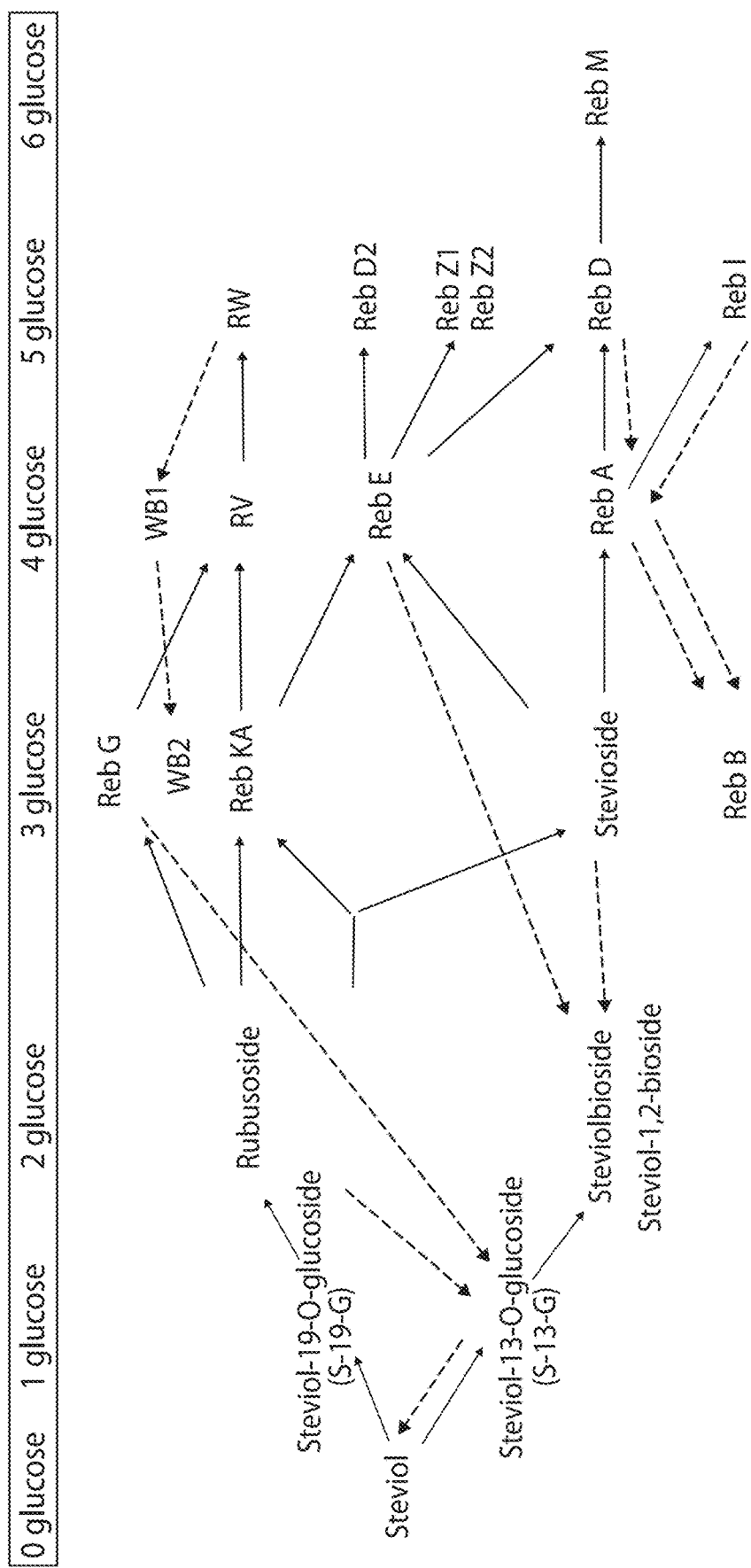
FIG. 9 shows that B-Glu1 can hydrolyze different steviol glycoside substrates. Black line: glycosylation; Dotted line: hydrolysis.

Using this technique we have hydrolyzed Reb M to remove Reb A, Reb D3, Reb D4, Reb W, Reb V, Reb E, Reb I and Reb D to increase purification efficacy (FIG. 9). This technique involves the use of stevioside and Reb A to produce steviol, steviol-13-O-glucoside, steviolbioside and Reb B through beta-glucosidase bioconversion. Referring to FIG. 8, steviol glycosides were hydrolyzed by disrupted Pichia pastoris cells. The samples included a steviolbioside ("SB") and rebaudioside B ("B") standard. In our experiments stevioside was hydrolyzed by disrupted Pichia cells at 24 hours; Reb E and Reb A were hydrolyzed by disrupted Pichia cells at 24 hours. Likewise, Reb I and Reb D were hydrolyzed by disrupted Pichia cells at 24 hours (FIG. 8).

Figure 10:
FIG. 10 shows a synthetic pathway for producing Reb M and Reb WB2.

In another embodiment of the current disclosure we can use beta-glucosidase to control steviol glycoside production pathways. (Ex: Reb M from Reb W) (FIG. 10).

According to preferred embodiments of the current disclosure the beta-glucosidase can be used to hydrolyze additional steviol glycosides including Reb V, Reb W, Reb Z1, Reb Z2, Reb D3 and Reb D4 to drive them to steviol glycosides of interest (FIG. 9). Thereafter we can separate, collect and concentrate the hydrolyzed products. In another embodiment of the current disclosure we use a beta-glucosidase deficient strain, which will reduce side production in our bioconversion process.

TABLE 1

Summary of hydrolysis of steviol glycosides by B-glu1.

| Substrate | Products |
|---|---|
| Rub | Steviol-13-O-glucoside (S-13-G), steviol |
| Stevioside | Steviolbioside (SB) |
| Reb E | stevioside, Steviolbioside (SB) |
| Reb A | Reb B |
| Reb 1 | Reb A, Reb B |
| Reb D | Reb B |
| Reb G | Steviol-13-O-glucoside (S-13-G), steviol |
| Reb B | No cleavage |
| Reb M | No cleavage |

STATEMENT OF INDUSTRIAL APPLICABILITY/TECHNICAL FIELD

This disclosure has applicability in the food, feed, beverage, and pharmacological industries. This disclosure relates generally to a method for the steviol glycosides biosynthesis via hydrolysis of beta glucosidase.

LITERATURE CITED AND INCORPORATED BY REFERENCE

1. Brandle, J. E. et al., (1998). *Stevia Rebaudiana: Its Agricultural, Biological, and Chemical Properties*, CANADIAN J. PLANT SCIENCE. 78 (4): 527-36.

2. Ceunen, S., and J. M. C. Geuns, *Steviol Glycosides: Chemical Diversity, Metabolism, and Function*, J. NAT. PROD., 2013, 76 (6), pp 1201-28 (2013).

3. Du J et al., (2011), *Engineering microbial factories for synthesis of value-added products*, J IND MICROBIOL BIOTECHNOL. 38: 873-90.

4. GRAS Notices, USA Food and Drug Administration, United States Health & Human Services. (2016) (relevant to steviol glycosides & polyglycosides).

5. Häusler A, and Münch T., (1997), *Microbial production of natural flavors*, ASM NEWS 63:551-59.

6. Prakash I., et al.; *Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia rebaudiana Morita*, BIOMOLECULES, 2014 June; 4(2): 374-89. (Published online 2014 Mar. 31, 2014).

7. Prakash I., et al., Development of Next Generation *Stevia* Sweetener: Rebaudioside M, FOODS, 2014, 3:162-175.

8. Shockey J M. Et a., (2003), *Arabidopsis contains a large superfamily of acyl-activating enzymes: phylogenetic and biochemical analysis reveals a new class of acyl-coenzyme A synthetases*. PLANT PHYSIOL 132 1065-76.

Sequences of Interest

```
Sequences:
B-glu1:
B-glu1 Amino Acid: (SEQ ID NO: 1) Pichia pastoris sequence (GS115)
Mtqldvesliqeltlnekvqllsgsdfwhttpvrrlgipkmrlsdgpngvrgtkffngvptacfpcgtglgatfdkellkeagslmad
eakakaasvvlgptaniargpnggrgfesfgedpvvnglssaaminglqgkyiaatmkhyvcndlemdrncidaqvshralrev
yllpfqiavrdanpraimtaynkangehvsqskflldevlrkewgwdgllmsdwfgvydakssitngldlempgppqcrvhsa
tdhainsgeihindvdervrsllslinychqsgvteedpetsdnntpetieklrkisresivllkdddrnrsilplkksdkiavignnak
qaaycgggsasvlsyhtttpfdsiksrledsntpaytigadayknlpplgpqmtdsdgkpgfdakffvgsptskdrklidhfqltns
qvflvdyyneqipenkefyvdvegqfipeedgtynfgltvfgtgrlfvddklvsdssqnqtpgdsffglaaqevigsihlvkgkay
kikvlygssvtrtyeiaasvafeggaftfgaakqrnedeeiaraveiakandkvvlciglnqdfesegfdrpdikipgatnkmvsav
lkanpntvivnqtgtpvempwasdapvilqawfggseagtaiadvlfgdynpsgkltvtfplrfednpaylnfqsnkqacwyge
dvyvgyryyetidrpvlfpfghglsftefdftdmfvrleeenlevevvvrntgkydgaevvqlyvapvspslkrpikelkeyakifl
asgeaktvhlsvpikyatsffdeyqkkwcsekgeytillgsssadikvsqsitlekttfwkgl B-glu1 DNA: (SEQ ID NO: 2) (codon optimized for E. coli)
ATGACCCAACTGGATGTGGAGAGCCTGATTCAAGAGCTGACCCTGAACGAAAAG
GTGCAACTGCTGAGCGGTAGCGACTTCTGGCATACCACCCCGGTTCGTCGTCTGG
GCATCCCGAAGATGCGTCTGAGCGACGGTCCGAACGGCGTTCGTGGTACCAAAT
TCTTTAACGGTGTTCCGACCGCGTGCTTCCCGTGCGGTACCGGTCTGGGCGCGAC
CTTTGACAAGGAACTGCTGAAAGAGGCGGGTAGCCTGATGGCGGATGAAGCGAA
AGCGAAAGCGGCGAGCGTGGTTCTGGGTCCGACCGCGAACATTGCGCGTGGTCC
GAACGGTGGCCGTGGCTTCGAGAGCTTCGGCGAGGACCCGGTGGTTAACGGTCT
GAGCAGCGCGGCGATGATCAACGGCCTGCAGGGCAAGTACATTGCGGCGACCAT
GAAACACTATGTTTGCAACGATCTGGAAATGGACCGTAACTGCATTGACGCGCA
AGTTAGCCACCGTGCGCTGCGTGAGGTGTACCTGCTGCCGTTCCAAATCGCGGTG
CGTGATGCGAACCCGCGTGCGATTATGACCGCGTATAACAAGGCGAACGGCGAA
CACGTTAGCCAGAGCAAATTCCTGCTGGACGAAGTGCTGCGTAAGGAGTGGGGC
TGGGATGGTCTGCTGATGAGCGACTGGTTTGGTGTTTACGATGCGAAAAGCAGCA
TCACCAACGGCCTGGACCTGGAGATGCCGGGTCCGCCGCAGTGCCGTGTGCACA
GCGCGACCGATCACGCGATCAACAGCGGCGAAATCCACATTAACGATGTTGACG
AGCGTGTGCGTAGCCTGCTGAGCCTGATTAACTACTGCCACCAAAGCGGTGTTAC
CGAGGAAGATCCGGAAACCAGCGACAACAACACCCCGGAAACCATCGAGAAGC
TGCGTAAAATCAGCCGTGAGAGCATTGTGCTGCTGAAGGACGATGACCGTAACC
GTAGCATTCTGCCGCTGAAGAAAAGCGACAAAATCGCGGTTATTGGTAACAACG
CGAAACAAGCGGCGTATTGCGGTGGCGGTAGCGCGAGCGTGCTGAGCTATCACA
CCACCACCCCGTTCGACAGCATCAAGAGCCGTCTGGAAGATAGCAACACCCCGG
CGTACACCATTGGTGCGGACGCGTATAAAAACCTGCCGCCGCTGGGTCCGCAAA
TGACCGATAGCGACGGCAAGCCGGGTTTTGATGCGAAATTCTTTGTTGGCAGCCC
GACCAGCAAGGATCGTAAACTGATCGACCACTTCCAGCTGACCAACAGCCAAGT
TTTTCTGGTGGACTACTATAACGAACAGATCCCGGAAAACAAGGAGTTCTACGTT
GACGTGGAGGGTCAATTTATTCCGGAGGAAGATGGCACCTATAACTTCGGTCTGA
CCGTGTTTGGTACCGGCCGTCTGTTCGTTGATGACAAACTGGTTAGCGACAGCAG
CCAGAACCAAACCCCGGGCGATAGCTTCTTTGGTCTGGCGGCGCAGGAAGTGAT
CGGCAGCATTCACCTGGTGAAGGGTAAAGCGTACAAGATCAAAGTTCTGTATGG
CAGCAGCGTGACCCGTACCTACGAAATTGCGGCGAGCGTTGCGTTTGAGGGCGG
```

```
TGCGTTCACCTTTGGTGCGGCGAAACAGCGTAACGAAGACGAGGAAATCGCGCG
TGCGGTGGAGATTGCGAAGGCGAACGACAAAGTGGTTCTGTGCATCGGCCTGAA
CCAAGATTTCGAAAGCGAGGGTTTTGATCGTCCGGACATCAAGATTCCGGGCGC
GACCAACAAAATGGTTAGCGCGGTGCTGAAGGCGAACCCGAACACCGTTATTGT
GAACCAGACCGGTACCCCGGTTGAGATGCCGTGGGCGAGCGATGCGCCGGTGAT
CCTGCAAGCGTGGTTTGGCGGTAGCGAGGCGGGTACCGCGATTGCGGATGTTCTG
TTTGGCGACTACAACCCGAGCGGCAAGCTGACCGTGACCTTCCCGCTGCGTTTTG
AGGATAACCCGGCGTACCTGAACTTCCAGAGCAACAAACAAGCGTGCTGGTATG
GCGAAGACGTTTACGTGGGTTATCGTTACTATGAGACCATCGATCGTCCGGTGCT
GTTCCCGTTTGGTCACGGCCTGAGCTTCACCGAGTTCGATTTTACCGACATGTTTG
TTCGTCTGGAGGAAGAGAACCTGGAAGTTGAGGTGGTTGTGCGTAACACCGGCA
AGTACGACGGTGCGGAAGTGGTGCAGCTGTATGTTGCGCCGGTTAGCCCGAGCC
TGAAACGTCCGATCAAGGAACTGAAAGAGTACGCGAAAATTTTCCTGGCGAGCG
GTGAAGCGAAGACCGTTCACCTGAGCGTGCCGATCAAATACGCGACCAGCTTCTT
TGATGAGTATCAAAAGAAATGGTGCAGCGAAAAGGGCGAGTATACCATTCTGCT
GGGTAGCAGCAGCGCGGACATCAAAGTTAGCCAAAGCATCACCCTGGAAAAAAC
CACCTTCTGGAAAGGTCTGTAA

B-glu2 Amino Acid: (SEQ ID NO: 3) Pichia pastoris sequence (GS115)
MKSQLIFMALASLVASAPLEHQQQHHKHEKRAVVTQTVTVAAGQTAAAGSAQAVV
TSSAAPASVASSAAASASSSSSSYTSGASGDLSSFKDGTIKCSEFPSGDGVVSVSWLGF
GGWSSIMNLQGGTSESCENGYYCSYACEAGYSKTQWPSNQPSDGRSVGGLLCKDGL
LYRSNTAFDTLCVPGKGTASVENNVSKGISICRTDYPGSENMCVPTWVDAGNSNTLT
VVDEDNYYEWQGLKTSAQYYVNNAGVSVEDGCIWGDESSGVGNWAPLVLGAGST
GGLTYLSLIPNPNNKKAPNFNVKIVATDGSSINGDCKYENGIFVGSSTDGCTVTVTSG
SAKLVFY B-glu2 DNA (SEQ ID NO: 4 ) Pichia pastoris sequence (GS115)
atgaaaagccagctgatctttatggctttggcctcccttgtagcaagtgcaccgctggaacaccagcagcagcatcataaacatgagaa
acgcgccgtagttacgcagacagtaactgttgcggcgggccagacagcagcagcgggttccgcccaggcagttgttacctcaagcg
cggcgccagcatccgttgcttcaagtgcggccgcgtctgctagctcatcttcttccagctatacctctgggcgttcaggcgatcttagtag
tttcaaagatggtactattaaatgttcagaattcccatcagggatggcgtggtgtccgtctcttggttaggcttcggcggctggtctagta
ttatgaatctgcagggtggtacttcagagagttgtgagaacggctattattgttcatatgcatgtgaagccggttatagcaaaacacagtg
gccatctaaccagccgtcagatgggagatcagtgggagggttgctgtgtaaagatggcctgttatatcgctccaatacagcgttcgata
cattatgtgtgcctgaaaaggtacagcatccgtggagaataatgtgtctcaaaggtatttccatttgtagaacggattatccggggtctga
aaacatgtgcgtcccgacgtgggtcgatgccggtaactcaaacaccttgacagtggtagatgaagataattattatgaatggcagggcc
ttaaaactagtgctcagtattatgtgaataacgccggtgttagtgttgaagatgggtgcatctggggcgatgagtccagcggcgttggaa
actgggcgccgttggttttgggggccggttccacgggggtctgacctatctgtctctgattccgaatcaaacaacaaaaaagcacc
gaattttaacgtaaaaatcgtggccacggatggaagttcaattaacggagattgcaaatatgaaaatgggatctttgtcggttcttcaacc
gatggctgcacggtaactgttacctcaggtagtgcaaaactggttttttattaa B-glu3 Amino Acid (SEQ ID NO: 5 ) Pichia pastoris sequence (GS115)
Mqvksivnlllacslavarplehahhqhdkrgyvvvtktivvdgstveataaaqvqehaetfaestpsavvssssapssassasap
assgsfsagtkgvtyspyqagggcktaeevasdlsqltgyeiirlygvdcnqvenvfkakapgqklflgiffvdaiesgvsaiasav
ksygswddvhtvsvgnelvnngeatvsqigqyvstaksalrsagftgpvlsvdtfiavinnpglcdfadeyvavnahaffdggiaa
sgagdwaaeqiqrvssacggkdvlivesgwpskgdtngaavpsksnqqaavqslgqkigsscyiafnafndywkadgpfnaek
ywgilds B-glu3 DNA (SEQ ID NO: 6) Pichia pastoris sequence (GS115)
Atgcaggttaaatctattgttaatttactgcttgcctgttccttggctgtggcgcgtccgttggaacacgctcaccatcagcatgataaacg
cggcgttgtagtagtaacgaaaaccatcgtcgttgatggtagcacagctaacgccgctgctcaggtgcaggagcatgcaga
aacctttgcagaatcaaccccgtcagccgtcgtttccagttcatccgcccttcatcagcaagctcagcttccgctccagctagttcaggt
tctttttcagctggtaccaaaggcgtgacatattccatatcaggccggtggtgggtgtaaaacagcggaagaagtggcatccgatctg
tcacagcttaccggttatgaaattattcggctttatggcgtagattgcaaccaggttgagaacgtgtttaaagccaaagcccctggccag
aaacttttttgggtatcttttttgtggatgccatcgagtctggcgtatcagctatcgcaagtgccgttaaatcctatggttcttgggatgatgt
acacactgtatctgttggcaacgagctggtgaacaatggcgaagccactgttagccagattggacatgttagtacggccaaatcag
ccttacgctctgccggtttcacagggccagtattgtctgttgatactttattgcagtgattaacaatccggggctgtgtgatttcgcggatg
aatatgttgctgtgaacgcccatgcgttcttcgatggggtattgctgcctcaggggcgggcgattgggcggcagagcagatccagcg
cgtctccagtgcgtgcggcgggaaagatgtcttaattgtagaaagcggttggccgtctaaaggagatacgaacggcgccgcagtgcc
gtcaaaatccaatcagcaggctgcagtccagagtcttggccagaagatgggagctcatgcattgccttaacgcatttaatgattattgg
aaagccgatggtccgttcaacgccgaaaaatattgggggatccttgatagttaa B-glu4 Amino Acid (SEQ ID NO: 7) Pichia pastoris sequence (GS115)
mlstilnifilllfiqaslqapipvvtkyvtegiavvtetnvrvvtktipivqvlisdgatythtlttvstaeengnfqpitttsivnkevvv
ptsvtpntqqtrptqvdttqnnadtpaaptpspttssnngvfttysttrsvvtsvvvvgpdgspientgqtanpttttapttsttaarttssts
tttptasstpggnhprsivyspysdssqckdattietdlefiaskgisavriygndcnyltvvlpkcaslglkvnqgfwigpsgvdsid
davqefiqavngnngfnwdlfelitvgneaisagyvsasslliskikevssilssagytgpittaeppnvyedygdlcstdvmsivgv
nahsyfntlfaasdsgsfyksqievvqkacsrsditiietgypsqgatngknvpskenqktaifsifevvgtdvtilstyddlwkdpg
pygieqffgaidlfs B-glu4 DNA (SEQ ID NO: 8) Pichia pastoris sequence (GS115)
atgctgtccacaattctgaatattttattcttctgttattcatccaggcgcctcttcaggcgcctattccggtggtgaccaaatatgtgaccga
aggtattgccgttgtgactgaaaccaatgtgcgggttgttactaaaaccattccgattgtgcaggtgctgatctccgatggtgcaacctat
actcatacccctgacgacagtgtcaacggcggaagaaaatggcaacttccagcctattaccacgacatctattgtcaacaaagaagttgt
agtaccaacaagcgtaaccccgaatacccagcagacgcgtccgacccaggtagatacccacacagaacaatgcggatacaccagcg
gcgcctcaccatcacctactactagttcaaacaacggcgtgttcaccacaacgagtactacacgaagcgtcgtcactagttcagtcgta
gtcggaccggatggaagccctattgaaaatactggacagcaaacccctactacaactgccccaactacaagctactgctgcc
cggaccacaagcagtacgtccaccacacctaccgctagctctacgccaggaggtaatcatccactagcatcgtctattctccatattc
cgatagcagtcagtgtaaagatgcgacaacgatcgaaaccgatcttgagttcattgcctctaaaggcatcagcgcggtacgtatttatgg
caatgattgtaactatcttacagttgtttttgcctaaatgtgccagtctgggattaaaagtgaatcagggcttttggattggtccaagtggagt
agatagcatcgatgatgcagtacaggagttattcaggcagtcaacggcaacaacggctttaattgggatttattcgaattaattaccgtc
```

-continued

```
ggaaacgaagcaatcagtgccggttatgtttcagcgagctccctgatttccaaaattaaagaagtatctagcattctgagctccgcgggt
tatactggtccaattaccacagccgaaccgcctaacgtatatgaggattatggcgatctgtgctcaaccgatgtaatgtccatcgtgggt
gtaaacgcgcattcctattttaatacccttttttgcggcctccgattcaggttcatttgtgaaatcacagatcgaagtagtccagaaagcatg
ctcacgttccgatattactattattgaaaccgggtatccgtcccagggagctaccaatggaaaaaacgttcctagtaaagagaatcagaa
aacagcgattttttcaatctttgaggtcgttggaacagatgtaactattcttagtacttatgatgatttgtggaaagatcctggaccgtatggg
attgaacagttttttggtgcgatcgatctttttttcttaa
```

---

What is claimed is:

1. A method of altering the glycosylation of a steviol glycoside, said method comprising:
   (a) exposing a first steviol glycoside to a *Pichia* sp. beta-glucosidase for sufficient time to generate a second steviol glycoside through the removal of at least one glucosyl group at the C19 position from said first steviol glycoside; and
   (b) collecting said second steviol glycoside.

2. The method of claim 1, wherein said first steviol glycoside is rubusoside and a glucosyl group is removed from the C19 position of said rubusoside to produce steviol-13-glucoside.

3. The method of claim 1, wherein said first steviol glycoside is stevioside and a glucosyl group is removed from the C19 position of said stevioside to produce steviolbioside.

4. The method of claim 1, wherein said first steviol glycoside is Reb E and a glucosyl group is removed from the C19 position of said Reb E to produce stevioside.

5. The method of claim 1, wherein said first steviol glycoside is Reb I and a glucosyl group is removed from the C19 position of said Reb I to produce Reb A.

6. The method of claim 1, wherein said first steviol glycoside is Reb A and a glucosyl group is removed from the C19 position of said Reb A to produce Reb B.

7. The method of claim 5, wherein further a glucosyl group is removed from the C19 position of said Reb A to produce Reb B.

8. The method of claim 1, wherein said first steviol glycoside is Reb D and two glucosyl groups are removed from the C19 position of said Reb D to produce Reb B.

9. The method of claim 1, wherein said first steviol glycoside is Reb G and a glucosyl group at the C19 position and a glucosyl group at the C13 position are removed from said Reb G to produce steviol-13-glucoside.

10. The method of claim 9, wherein further a glucosyl group is removed from the C13 position of said steviol-13-glucoside to produce steviol.

11. The method of claim 1, wherein said second steviol glycoside is Reb B.

12. The method of claim 1, wherein said first steviol glycoside Reb A.

13. The method of claim 1, further comprising the use of beta-galactosidase or pectinase enzymes to increase the speed of enzymatic hydrolysis.

14. The method of claim 1, wherein the beta-glucosidase has an amino acid sequence that has at least 90% identity to SEQ ID NO:1.

15. The method of claim 1, wherein the beta-glucosidase has an amino acid sequence that is at least 95% identical to SEQ ID NO:3.

16. The method of claim 1, wherein exposing said first steviol glycoside to the beta-glucosidase comprises exposing said first steviol glycoside to disrupted *Pichia* cells thereby releasing said *Pichia* sp. beta-glucosidase from the *Pichia* cells.

17. The method of claim 2, wherein further a glucosyl group is removed from the C13 position of said steviol-13-glucoside to produce steviol.

18. The method of claim 4, wherein further a glucosyl group is removed from the C19 position of said stevioside to produce steviolbioside.

* * * * *